US006921766B1

(12) United States Patent
Fukami et al.

(10) Patent No.: US 6,921,766 B1
(45) Date of Patent: **\*Jul. 26, 2005**

(54) BLOOD VESSEL LIPID DEPOSITION-PREVENTIVE AGENT COMPRISING CHYMASE-INHIBITOR

(75) Inventors: Harukazu Fukami, Kyoto (JP); Hidenori Urata, Fukuoka (JP)

(73) Assignee: Daiichi Suntory Pharma Co., Ltd., Tokyo (JP)

(*) Notice: Subject to any disclaimer, the term of this patent is extended or adjusted under 35 U.S.C. 154(b) by 118 days.

This patent is subject to a terminal disclaimer.

(21) Appl. No.: 09/869,360
(22) PCT Filed: Nov. 1, 2000
(86) PCT No.: PCT/JP00/07706
§ 371 (c)(1),
(2), (4) Date: Jun. 28, 2001
(87) PCT Pub. No.: WO01/32214
PCT Pub. Date: May 10, 2001

(30) Foreign Application Priority Data

Nov. 1, 1999 (JP) .......................................... 11/311257

(51) Int. Cl.[7] ............................................. A61K 31/513
(52) U.S. Cl. ................................ 514/266.3; 514/266.2; 544/284; 544/285
(58) Field of Search .................... 514/266.2, 266.3, 514/266.31; 544/284, 285

(56) References Cited

U.S. PATENT DOCUMENTS

| | | | | |
|---|---|---|---|---|
| 5,691,335 | A | | 11/1997 | Fukami et al. ............ 514/235.8 |
| 5,814,631 | A | | 9/1998 | Fukami et al. ............ 514/234.5 |
| 5,948,785 | A | * | 9/1999 | Akahoshi et al. ........... 514/269 |
| 6,080,738 | A | * | 6/2000 | Akahoshi et al. ......... 514/227.8 |
| 6,300,337 | B1 | * | 10/2001 | Ishida et al. ................. 514/269 |
| 6,432,978 | B1 | * | 8/2002 | Tani et al. ................... 514/312 |

FOREIGN PATENT DOCUMENTS

| | | | |
|---|---|---|---|
| EP | 0 795 548 | | 9/1997 |
| JP | 05 169832 | | 7/1993 |
| JP | 10-053579 | * | 2/1998 |
| WO | 93/03625 | | 3/1993 |
| WO | 93/25574 | | 12/1993 |
| WO | 96/04248 | | 2/1996 |
| WO | 96/33974 | | 10/1996 |
| WO | 96/39373 | | 12/1996 |
| WO | 97/11941 | | 4/1997 |
| WO | 97/45400 | | 12/1997 |
| WO | 98/18794 | | 5/1998 |
| WO | 99/41277 | | 8/1999 |
| WO | 00/10982 | | 3/2000 |
| WO | WO-00/32587 | * | 6/2000 |

OTHER PUBLICATIONS

Jozef Oleksyszyn et al, "Irreversible Inhibition of Serine Proteases by Peptide Derivatives of (α–Aminoalkyl)phosphonate Diphenyl Esters" Biochemistry, Jan. 15, 1991, 30, pp. 485–493.

Hidenori Urata et al, "Cloning of the Gene and cDNA for Human Heart Chymase" Biol. Chem., Sep. 15, 1991, vol. 266, No. 26, pp. 17173–17179.

Margarita Bastos, et al, "Inhibitors of human heart chymase based on a peptide library" Proc. Natl. Acad. Sci., vol. 92, Jul. 1995, pp. 6738–6742.

Jorma O. Kokkonen, et al, "Role of Mast Cell Proteases and Proteoglycans in Lipoprotein Metabolism" *Mast Cell Proteases in Immunology and Biology*, pp. 257–287, 1995.

Suguru Nakayama, et al, "Pathophysiological roles of human chymase" Nippon Rinsho, Aug. 1997, 55(08); pp. 1903–1908.

Shinji Takai, et al, "Induction of chymase that forms angiotensin II in the monkey atherosclerotic aorta", FEBS Letters, Jul. 21, 1997, 412(1), pp. 86–90.

Maki Akasu, et al, "Differences in Tissue Angiotensin II–Forming Pathways by Species and Organs in Vitro" Hypertension, Sep. 1998, 32(3); pp. 514–520.

Jason L. Johnson, "Activation of Matrix–Degrading Metalloproteinases by Mast Cell Proteases in Atherosclerotic Plaques" Arterioscler Thromb Vasc Biol, Nov. 1998, 18(11), pp. 1707–1715.

Shlomo Keidar, "Angiotensin, LDL Peroxidation and Atherosclerosis" Life Sciences, 1998, vol. 63, No. 1, pp. 1–11.

(Continued)

*Primary Examiner*—Richard L. Raymond
(74) *Attorney, Agent, or Firm*—Burns, Doane, Swecker & Mathis, L.L.P.

(57) ABSTRACT

There is provided a preventive or therapeutic agent for diseases accompanied by abnormal vascular function in which lipid deposition in the blood vessel is involved, said agent comprising a chymase inhibitor as an active ingredient.

As the chymase inhibitor, a quinazoline derivative represented by the following formula is used.

(1)

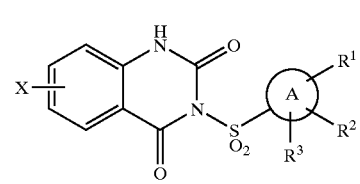

In the above formula, the ring A represents an aromatic ring.

3 Claims, 3 Drawing Sheets

OTHER PUBLICATIONS

Masanori Yoshizumi, et al, "Effects of endothelin–1 (1–31) on extracelular signal–regulated kinase and proliferation of human coronary artery smooth muscle cells" British Journal of Pharmacology, 1988), 125, pp. 1019–1027.

Masanori Yoshizumi, et al, "Endothelin–1–(1–31), a novel vasoactive peptide, increases $[Ca^{2+}]_i$ in human coronary artery smooth muscle cells" European Journal of Pharmacology 348, 1998, pp. 305–309.

Makoto Ihara, et al, "Increased Chymase–Dependent Angiotensin II Formation in Human Atherosclerotic Aorta" Hypertension, Jun. 1999, 33(6), pp. 1399–1405.

Y. Liao, et al., "The chymase–angiotensin system in humans: Biochemistry, molecular biology and potential role in cardiovascular diseases", Canadian Journal of Cardiology, vol. 11, No. Suppl. F., pp. 13F–19F, Aug. 1995.

S. Niwata et al., "Substituted 3–(Phenylsulfonyl)–1–phenylimidazolidine–2,4–dione Derivatives as Novel Nonpeptide Inhibitors of Human Heart Chymase", Journal of Medicinal Chemistry, vol. 40, No. 14, 1997, pp. 2156–2163.

H. Fukami et al, "Chymase: Its Pathophysiologic Roles and Inhibitors," Current Pharmaceutical Design, vol. 4, No. 6, pp. 439–453, 1998.

K. Paananen et al, "Proteolysis and Fusion of Low Density Lipoprotein Particles Independently Strengthen The Binding to Exocytosed Mast Cell Granules", Journal of Biological Chemistry, vol. 269, No. 3, pp. 2023–2031, 1994.

H. Bult et al, "Antiatherosclerotic activity of drags in relation to nitric oxide function", European Journal of Pharmacology, vol. 375, Issue 1–3), pp. 157–176, Jun. 30, 1999.

* cited by examiner

BLOOD VESSEL LIPID DEPOSITION-PREVENTIVE AGENT COMPRISING CHYMASE-INHIBITOR

TECHNICAL FIELD

The present invention provides a preventive or therapeutic agent for diseases accompanied by abnormal vascular function in which lipid deposition in the blood vessel is involved, a preventive or therapeutic pharmaceutical composition for diseases accompanied by abnormal vascular function, and a suppressing agent of lipid deposition in the blood vessel.

BACKGROUND ART

A major mechanism of lipid deposition in the blood vessel is believed that monocytes and macrophages infiltrate into the injured vascular endothelial cells, and thereby these cells incorporate oxygenated low density lipoproteins (LDL) in excess and turn into the so-called foam cells that have accumulated droplets of cholesterol esters (Ross R., Nature 362: 801, 1993). It is thought that foam cells, together with T cells and vascular smooth muscle cells, form fatty streaks, and the interaction between the cells facilitates pathological processes, generating vascular lesions such as arteriosclerosis including atherosclerosis.

In many epidemiological studies in recent years, hyperlipemia has been defined as a risk factor of arteriosclerosis, and in fact various drugs that regulate blood levels of lipids such as cholesterol and triglyceride have been reported. For example, drugs such as Plavastatin that suppress cholesterol biosynthesis by inhibiting 3-hydroxy-3-methylglutaryl coenzyme A (HMG-CoA) have been widely used. These drugs can indeed lower lipid levels in the blood during the administration period, but various problems have been pointed out: once the administration is suspended the level returns to the level before administration; the effect is not adequate in patients with severe high-cholesterolemia; or improvement in blood lipid levels does not always lead to life lengthening.

These drugs are also known to be associated with side effects such as myopathy and abnormal hepatic function, and are likely to inhibit the biosynthesis of physiological components such as ubiquinone and dolichol, raising a possibility to elicit an adverse effect. Other therapeutic agents of hyperlipemia include drugs that influence lipoprotein metabolism in the blood vessel such as Clofibrate, drugs that suppress the absorption of cholesterol from the intestinal tract such as Nicomol and Colestyramine, and the like. None of them, however, are satisfactory in terms of efficacy and side effects, and thus there is a need for the development of further excellent drugs in terms of efficacy and safety.

On the other hand, chymase is a serine protease that is widely distributed in the tissue such as the skin, the heart, vascular walls, intestinal tracts, etc. as a granular component in mast cell (Mast Cell Proteases in Immunology and Biology; Caughey, G. H., Ed; Marcel Dekker, Inc.: New York, 1995). Chymase is known to participate in a synthetic process independent of angiotensin converting enzyme in the conversion of angiotensin I to angiotensin II.

It is also reported that in the aorta of atherosclerosis or arterial aneurysm a chymase-dependent angiotensin II (AngII) forming activity was observed to be significantly higher than in the aorta without atherosclerosis or arterial aneurysm (M. Ihara, et al., Hypertension 32: 514–20, 1998) and that the expression of chymase mRNA is increased in the aorta of monkeys that were fed a high-cholesterol diet for 6 months (S. Takai, et al., FEBS Lett. 412: 86–90, 1997).

It has also been indicated that LDL can be restrictively degradated by chymase, and that the modified LDL binds to mast cell granules (Mast Cell Proteases in Immunology and Biology; Caughey, G. H., Ed; Marcel Dekker, Inc.: New York, 1995). LDL-granule complex is likely to be easily incorporated into macrophages. These clinical findings and experimental results implicate the involvement of intravascular chymase in atheroma formation, but the nole of chymase in pathological and physiological states has not been elucidated and the study to clarify this point has just begun. In recent years, search for substances that inhibit chymase activity are underway in addition to the elucidation of physiological actions of chymase.

As chymase inhibitors, there have been reported: a low molecular weight chymase inhibitor described in a textbook (Protease Inhibitors; Barrett et al., Eds.: Elssevier Science B.V.: Amsterdam, 1996); reported as a peptidyl inhibitor, α-keto acid derivative (WO 93-25574, Proc. Natl. Acad. Sci. USA 92: 6738, 1995), α,α-difluoro-β-keto acid derivative (Japanese Unexamined Patent Publication (Kokai) No. 9-124691), a tripeptide inhibitor (WO 93-03625), and a phosphoric acid derivative (Oleksyszyn et al., Biochemistry 30: 485, 1991); as peptide-like inhibitors, a trifluoromethylketone derivative (WO 96-33974, Japanese unexamined Patent Publication (Kokai) No. 10-53579) and an acetamide derivative (Japanese Unexamined Patent Publication (Kokai) No. 10-7661, Japanese Unexamined Patent Publication (Kokai) No. 10-53579, Japanese Unexamined Patent Publication (Kokai) No. 11-246437, WO 99-41277, WO 98-18794, WO 96-39373); as non-peptidyl inhibitors, a triazine derivative (Japanese Unexamined Patent Publication (Kokai) No. 8-208654, Japanese Unexamined Patent Publication (Kokai) No. 10-245384), a phenolester derivative (Japanese Unexamined Patent Publication (Kokai) No. 10-87567), a cephem derivative (Japanese Unexamined Patent Publication (Kokai) No. 10-87493), an isoxazole derivative (Japanese Unexamined Patent Publication (Kokai) No. 11-1479), an imidazolidine derivative (WO 96-04248), a hydantoin derivative (Japanese Unexamined Patent Publication (Kokai) No. 9-31061), a quinazoline derivative (WO 97-11941), and the like. However, no drugs or therapeutic regimens have been established that employ the inhibition of chymase activity as a therapeutic strategy.

DISCLOSURE OF THE INVENTION

The present invention intends to provide a safe preventive or therapeutic agent that suppresses the progression of pathological processes in abnormal vascular function in which lipid deposition is involved and prevents the progression of various complications, which will improve the quality of life of the patients.

After intensive study to resolve the above problems, the inventors of the present invention have created an animal model of arterial lipid deposition induced by a high-cholesterol diet, obtained a finding that, surprisingly, a chymase inhibitor suppresses lipid deposition in the blood vessel and improves abnormal vascular function, and clarified the association of chymase activity with lipid deposition, and thereby have completed the present invention.

Thus, the present invention relates to a preventive or therapeutic agent for diseases accompanied by abnormal vascular function in which lipid deposition in the blood vessel is involved, said agent comprising a chymase inhibitor as an active ingredient.

The present invention also relates to a preventive or therapeutic pharmaceutical composition for diseases accompanied by abnormal vascular function, wherein the chymase inhibitor is blended at an amount that suppresses lipid deposition in the blood vessel.

Furthermore, the present invention relates to a suppressing agent of lipid deposition in the blood vessel, comprising a chymase inhibitor as an active ingredient.

EMBODIMENT FOR CARRYING OUT THE INVENTION

As used herein, diseases accompanied by abnormal vascular function in which lipid deposition in the blood vessel is involved include diseases that result from abnormal vascular function caused by lipid deposition in the blood vessel, diseases of which symptoms are aggravated by the development of abnormal vascular function caused by lipid deposition in the blood vessel, diseases of which cure is delayed by the development of abnormal vascular function caused by lipid deposition in the blood vessel and the like. For example, the onset of abnormal vascular function associated with lipid deposition in the blood vessel is observed in arteriosclerosis, cardiac acute coronary syndrome such as unstable angina, and acute myocardial infarction, restenosis after percutaneous transluminal coronary angioplasty, obstructive arteriosclerosis, obstructive thrombotic vasculitis, atherosclerosis, cerebral infarction, intermittent claudication, lower limb gangrene, renal vascular hypertension, renal arterial aneurysm, renal infarction, and the like.

Chymase inhibitors suitable for use in the present invention can be selected as substances that can inhibit chymase activity by using methods capable of being performed by a person skilled in the art. As a method of selection, there can be mentioned a method described in Example 1 below. The compounds obtained in this way include, for example, a low molecular weight chymase inhibitor described in a textbook (Protease Inhibitors; Barrett et al., Ed.: Elssevier Science B.V.: Amsterdam, 1996); reported as a peptidyl inhibitor, α-keto acid derivative (WO 93-25574, Proc. Natl. Acad. Sci. USA 92: 6738, 1995), α,α-difluoro-β-keto acid derivative (Japanese Unexamined Patent Publication (Kokai) No. 9-124691), a tripeptide inhibitor (WO 93-03625), and a phosphoric acid derivative (oleksyszyn et al., Biochemistry 30: 485, 1991); as a peptide-like inhibitor, a trifluoromethylketone derivative (WO 96-33974, Japanese Unexamined Patent Publication (Kokai) No. 10-53579) and an acetamide derivative (Japanese Unexamined Patent Publication (Kokai) No. 10-7661, Japanese Unexamined Patent Publication (Kokai) No. 10-53579, Japanese Unexamined Patent Publication (Kokai) No. 11-246437, WO 99-41277, WO 98-18794, WO 96-39373); as non-peptidyl inhibitors, a triazine derivative (Japanese Unexamined Patent Publication (Kokai) No. 8-208654, Japanese Unexamined Patent Publication (Kokai) No. 10-245384), a phenolester derivative (Japanese Unexamined Patent Publication (Kokai) No. 10-87567), a cephem derivative (Japanese Unexamined Patent Publication (Kokai) No. 10-87493), an isoxazole derivative (Japanese Unexamined Patent Publication (Kokai) No. 11-1479), an imidazolidine derivative (WO 96-04248), a hydantoin derivative (Japanese Unexamined Patent Publication (Kokai) No. 9-31061), a quinazoline derivative (WO 97-11941), and the like, and as a representative example of preferred chymase inhibitors, there can be mentioned a compound represented by the following formula (1):

wherein, the ring A represents an aryl ring, $R^1$ represents a hydroxy group, an amino group, or a lower alkylamino group having 1 to 4 carbons that may be substituted with a carboxylic group, a lower aralkylamino group having 7 to 10 carbons that may be substituted with a carboxylic group, an amino group acylated with a lower fatty acid having 1 to 4 carbons that may be substituted with a carboxylic group, an amino group acylated with an aromatic carboxylic acid that may be substituted with a carboxylic group, an amino group acylated with a heteroaromatic carboxylic acid that may be substituted with a carboxylic group, an amino group sulfonylated with a lower alkanesulfonic acid having 1 to 4 carbons that may be substituted with a carboxylic group, an amino group sulfonylated with an aromatic sulfonic acid that may be substituted with a carboxylic group, an amino group sulfonylated with a heteroaromatic sulfonic acid that may be substituted with a carboxylic group, a lower alkyl group having 1 to 4 carbons substituted with a carboxylic group, or a lower alkylene group having 2 to 4 carbons substituted with a carboxylic group;

$R^2$ and $R^3$, which may be the same or different, represent a hydrogen, a lower alkyl group having 1 to 4 carbons that may be substituted, a halogen atom, a hydroxy group, a lower alkoxy group having 1 to 4 carbons, an amino group, a lower alkylamino group having 1 to 4 carbons that may be substituted, a lower aralkylamino group having 7 to 10 carbons that may be substituted, an amino group acylated with a lower fatty acid having 1 to 4 carbons that may be substituted with a carboxylic group, an amino group acylated with an aromatic carboxylic acid that may be substituted with a carboxylic group, an amino group acylated with a heteroaromatic carboxylic acid that may be substituted with a carboxylic group, an amino group sulfonylated with a lower alkanesulfonic acid having 1 to 4 carbons that may be substituted with a carboxylic group, an amino group sulfonylated with an aromatic sulfonic acid that may be substituted with a carboxylic group, an amino group sulfonylated with a heteroaromatic sulfonic acid that may be substituted with a carboxylic group, or a carboxylic group; or when the ring A is a benzene ring, $R^1$ and $R^2$, together with the benzene ring to be substituted, may form a fused heterocyclic ring that may be substituted with a carboxylic acid, and a carbon atom in said fused heterocyclic ring may form a carbonyl group wherein $R^3$ is as defined above; and X represents a hydrogen atom, a lower alkyl group having 1 to 4 carbons, a lower alkoxy group having 1 to 4 carbons, a halogen atom, a hydroxy group, an amino group, or a nitro group;

and a pharmaceutically acceptable salt thereof.

As a preferred example of the aryl ring represented by the ring A in the general formula (1), a benzene ring or a naphthalene ring is illustrated.

As a preferred example of $R^1$ which is a lower alkylamino group having 1 to 4 carbons that may be substituted with a carboxylic group or a lower aralkylamino group having 7 to 12 carbons that may be substituted with a carboxylic group, there can be illustrated a methylamino group, an ethylamino group, a propylamino group, a butylamino group, a carboxymethylamino group, a carboxyethylamino group, a carboxypropylamino group, a carboxybutylamino group, a benzylamino group, a phenethylamino group, a phenylpropylamino group, a phenylbutylamino group, a carboxybenzylamino group, a carboxyphenethylamino group, a carboxyphenylpropylamino group, a carboxyphenylbutylamino group, and the like.

As a preferred example of $R^1$ which is an amino group acylated with a lower fatty acid having 1 to 4 carbons that may be substituted with a carboxylic group, an amino group acylated with an aromatic carboxylic acid that may be substituted with a carboxylic group, or an amino group acylated with a heteroaromatic carboxylic acid that may be substituted with a carboxylic group, there can be illustrated a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, a carboxypyrrolecarbonylamino group, and the like.

As a preferred example of $R^1$ which is an amino group sulfonylated with a lower alkanesulfonic acid having 1 to 4 carbons that may be substituted with a carboxylic group, an amino group sulfonylated with an aromatic sulfonic acid that may be substituted with a carboxylic group, or an amino group sulfonylated with a heteroaromatic sulfonic acid that may be substituted with a carboxylic group, there can be illustrated a methanesulfonylamino group, an ethanesulfonylamino group, a propanesulfonylamino group, a butanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybutanesulfonylamino group, a carboxybenzenesulfonylamino group, a carboxynaphthalenesulfonylamino group, a carboxypyridinesulfonylamino group, a carboxypyrrolesulfonylamino group, and the like.

As a preferred example of $R^1$ which is a lower alkyl group having 1 to 4 carbons substituted with a carboxylic group, there can be illustrated an acetic group, propionic group, butyric group, valeric group, and the like. As a preferred example of $R^1$ which is a lower alkylene group having 2 to 4 carbons substituted with a carboxylic group, there can be illustrated an acrylic group, a crotonic group, and the like.

As a preferred example of $R^2$ or $R^3$ which is a lower alkyl group having 1 to 4 carbons that may be substituted, there can be illustrated a straight-chain alkyl group such as a methyl group, an ethyl group, a n-propyl group, and a n-butyl group, a branched-chain alkyl group such as an isopropyl group, a sec-butyl group, and a t-butyl group, and as a preferred example of the substituent of a lower alkyl group having 1 to 4 carbons, there can be illustrated a carboxylic group, a halogen atom such as fluorine and chlorine, a lower alkoxy group having 1 to 4 carbons, an amino group, a methylamino group, a dimethylamino group, a carboxymethylamino group, and a carboxyethylamino group and the like. As a preferred example of $R^2$ or $R^3$ which is a halogen atom, there can be illustrated fluorine, chlorine, and iodine.

As a preferred example of $R^2$ or $R^3$ which is a lower alkoxy group having 1 to 4 carbons, there can be illustrated a straight-chain alkyloxy group such as a methoxy group, an ethoxy group, a n-propyloxy group and a n-butoxy group, a branched-chain alkyloxy group such as an isopropyloxy group, a sec-butoxy group and a t-butoxy group.

As a preferred example of $R^2$ or $R^3$ which is a lower alkylamino group having 1 to 4 carbons that may be sutstituted, there can be illustrated a methylamino group, an ethylamino group, a propylamino group, a butylamino group, and the like, and as a preferred example of the substituent of the lower alkylamino group having 1 to 4 carbons, there can be illustrated a carboxylic group, a halogen atom such as fluorine and chlorine, a lower alkoxy group having 1 to 4 carbons, and the like.

As a preferred example of $R^2$ or $R^3$ which is a lower aralkylamino group having 7 to 12 carbons that may be sutstituted, there can be illustrated a benzylamino group, a phenethylamino group, a phenylpropylamino group, a phenylbutylamino group, and the like, and as a preferred example of the substituent of the aralkylamino group, there can be illustrated a carboxylic group, a halogen atom such as fluorine and chlorine, a lower alkoxy group having 1 to 4 carbons, and the like.

As a preferred example of $R^2$ or $R^3$ which is an amino group acylated with a lower fatty acid having 1 to 4 carbons that may be substituted with a carboxylic group, an amino group acylated with an aromatic carboxylic acid that may be substituted with a carboxylic group, or an amino group acylated with a heteroaromatic carboxylic acid that may be substituted with a carboxylic group, there can be illustrated a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, a carboxypyrrolecarbonylamino group, and the like.

As a preferred example of $R^2$ or $R^3$ which is an amino group sulfonylated with a lower alkanesulfonic acid having 1 to 4 carbons that may be substituted with a carboxylic group, an amino group sulfonylated with an aromatic sulfonic acid that may be substituted with a carboxylic group, or an amino group sulfonylated with a heteroaromatic sulfonic acid that may be substituted with a carboxylic group, there can be illustrated a methanesulfonylamino group, an ethanesulfonylamino group, a propanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybenzenesulfonylamino group, a carboxynaphthalenesulfonylamino group, a carboxypyridinesulfonylamino group, a carboxypyrrolesulfonylamino group, and the like.

When the ring A is a benzene ring, as a preferred example of a fused heterocyclic ring that is formed by $R^1$ and $R^2$ together with the benzene ring to be substituted, that may be substituted with a carboxylic acid, and whose carbon atom in the fused heterocyclic ring may form a carbonyl group, there can be mentioned a tetrahydroquinoline ring and a benzoxadine ring, and specifically there can be illustrated tetrahydroquinoline, benzoxadine, quinoxaline, benzodioxane, carboxytetrahydroquinoline, carboxybenzoxadine, carboxyquinoxaline, carboxybenzodioxane, and the like.

As a preferred example of X which is a lower alkyl group having 1 to 4 carbons, there can be illustrated a straight-chain alkyl group such as a methyl group, an ethyl group, a n-propyl group and a n-butyl group, and a branched-chain alkyl group such as an isopropyl group, a sec-butyl group and a t-butyl group. As a preferred example of X which is a lower alkoxy group having 1 to 4 carbons, there can be illustrated a straight-chain alkyloxy group such as a methoxy group, an ethoxy group, a n-propoxy group and a n-butoxy group, and a branched-chain alkyloxy group such as an isopropyloxy group, a sec-butoxy group and a t-butoxy group. As a preferred example of X which is a halogen atom, there can be illustrated fluorine, chlorine, bromine, or iodine.

As an example of pharmaceutically acceptable salts, there can be illustrated an acid addition salt such as a hydrochlorate, a methanesulfonate, a trifluoroacetate and a nitrate, and an alkali metal salt such as a sodium salt and a potassium salt.

The quinazoline derivative represented by the formula (1) of the present invention may be synthesized according to, for example, the synthetic method (A) or (B) shown below.

Synthetic Method (A)

A compound represented by the formula (2):

(2)

wherein, the ring A is as defined above, $R^{1'}$ represents $R^1$ that may be protected with a protecting group, $R^{2'}$ represents $R^2$ that may be protected with a protecting group, $R^{3'}$ represents $R^3$ that may be protected with a protecting group, and $R^1$, $R^2$ and $R^3$ are as defined above, is reacted with an anthranilic acid derivative represented by the formula (3):

(3)

wherein, X' represents X that may be protected with a protecting group, and X is as defined above, using a method, for example, described in Japanese Unexamined Patent Publication (Kokai) No. 6-199839, so as to obtain a sulfonylurea derivative represented by the formula (4):

(4)

wherein, A, $R^{1'}$, $R^{2'}$, $R^{3'}$, and X' are as defined above, and then using a condensation agent such as 1,1'-carbonyldiimidazole (hereinafter referred to as CDI), the quinazoline ring is closed, and if desired the protecting group of $R^1$, $R^2$, $R^3$ or X is deprotected. In this reaction, when $R^1$, $R^2$ or $R^3$ represents a group that contains a hydroxyl group, an amino group or a carboxylic group, $R^1$, $R^2$ or $R^3$ may be protected, if necessary, with a protecting group such as a benzyloxycarbonyl group, a t-butoxycarbonyl group, a benzyl group, an allyl group and a t-butyl group. When X represents a hydroxyl group or an amino group, it may be protected, if necessary, with a protecting group such as a benzyloxycarbonyl group, a t-butoxycarbonyl group, a benzyl group, an allyl group or a t-butyl group.

As a compound represented by the formula (2) for use in the present invention, a commercially available or known compound or a compound that can be synthesized by a known method may be used. For example, by the synthetic method described in EP 0269141, those that can be synthesized from the corresponding sulfonamide derivative using chlorosulfonyl isocyanate can be used. For example, 3-allyloxycarbonylmethylbenzenesulfonylisocyanate, 4-allyloxycarbonylmethylbenzenesulfonylisocyanate, 4-allyloxybenzenesulfonylisocyanate, and the like can be used.

As an anthranilic acid derivative represented by the formula (3) for use in the present invention, a commercially available or known compound or a compound that can be synthesized by a known method may be used. For example, anthranilic acid, 4-chloroanthranilic acid, 4-methoxyanthranilic acid, 5-chloroanthranilic acid, 4-hydroxyanthranilic acid, and the like can be used.

The reaction of closing a quinazoline ring from a sulfonylurea derivative represented by the formula (4) may be performed in an aprotic solvent, for example, an ethereal solvent such as tetrahydrofuran and dioxane, a halogenic solvent such as methylene chloride, or dimethylformamide, at a temperature between −50 and 50° C., preferably at a temperature between −20° C. and room temperature. For the cyclization reaction, a conventional dehydrocondensation agent such as CDI, dicyclohexylcarbodiimide (DCC), and a related carbodiimide compound, and a mixed acid anhydride can also be used. For the deprotection reaction, hydrolysis with an acid or an alkali, reduction, oxidation, etc. may be selected as appropriate.

Synthetic Method (B)

A compound represented by the formula (5):

wherein, ring A, $R^{1'}$, $R^{2'}$ and $R^{3'}$ are as defined above, is condensed with an anthranilic acid derivative represented by the formula (6):

wherein, X' is as defined above, Ph represents a phenyl group, R4 represents a protecting group of a carboxyl group, specifically a group that can be eliminated by hydrolysis or hydrogenolysis and that can form an ester group in combination with a carboxyl group, for example a methyl group, an ethyl group or a benzyl group, using, for example, 1,8-diazabicyclo[5,4,0]-7-undecene (hereinafter referred to as DBU), so as to obtain a compound represented by the formula (7):

wherein, ring A, $R^{1'}$, $R^{2'}$, $R^{3'}$, $R^4$ and X' are as defined above, which is then converted by alkali hydrolysis or hydrogenolysis into the corresponding carboxylic acid represented by the formula (4), and then, as in the synthetic method (A), the quinazoline ring is closed and if desired the protecting group of $R^1$, $R^2$, $R^3$ and X is deprotected. In this reaction, when $R^1$, $R^2$ or $R^3$ represents a group that contains a hydroxyl group, an amino group or a carboxylic group, $R^1$, $R^2$ or $R^3$ may be protected, if necessary, with a protecting group such as a benzyloxycarbonyl group, a t-butoxycarbonyl group, a benzyl group, an allyl group or a t-butyl group. When x represents a hydroxyl group or an amino group, it may be protected, if necessary, with a protecting group such as a benzyloxycarbonyl group, a t-butoxycarbonyl group, a benzyl group, an allyl group or a t-butyl group.

As a compound represented by the formula (5) for use in the present invention, a commercially available or known compound or a compound that can be synthesized by a known method may be used. For example, there can be used 3-hydroxybenzenesulfonamide, 2-aminobenzenesulfonamide, 3-aminobenzenesulfonamide, 4-aminobenzenesulfonamide, (±)-2-(4-aminosulfonylphenyl)butyrate, 3-benzyloxycarbonylamino-4-chlorobenzenesulfonamide, 4-benzyloxycarbonylamino-3-chlorobenzenesulfonamide, 4-amino-3,5-dichlorobenzenesulfonamide, 3-benzyloxycarbonylamino-4-methylbenzenesulfonamide, 4-t-butoxycarbonyl-3-hydroxybenzenesulfonamide, 3-benzyloxycarbonylamino-4-t-butoxycarbonylbenzenesulfonamide, 4-t-butoxycarbonyl-3-hydroxybenzenesulfonamide, 3-t-butoxycarbonyl-4-hydroxybenzenesulfonamide, 3-acetamide-4-methoxybenzenesulfonamide, 3-(3-aminosulfonyl)phenylacrylic acid t-butylester, 3-amino-4-methoxybenzenesulfonamide, 4-methoxy-3-methylsulfonylaminobenzenesulfonamide, 3-carboxy-4-hydroxy-2-naphthalenesulfonamide, 4-benzyloxycarbonylamino-3-t-butoxycarbonylbenzenesulfonamide, (±)-3-t-butoxycarbonyl-2-oxo-1H,3H-quinoline-7-sulfonamide, (±)-2-t-butoxycarbonyl-3-oxo-1,4-benzooxadine-6-sulfonamide, and the like.

As an anthranilic acid derivative represented by the formula (6) for use in the present invention, a commercially available or known compound or a compound that can be synthesized by a known method may be used. For example, there can be used methyl 4-chloro-2-N-phenoxycarbonylanthranilate, ethyl 4-chloro-2-N-phenoxycarbonylanthranilate, benzyl 4-chloro-2-N-phenoxycarbonylanthranilate, methyl 5-chloro-2-N-phenoxycarbonylanthranilate, ethyl 5-chloro-2-N-phenoxycarbonylanthranilate, benzyl 5-chloro-2-N-phenoxycarbonylanthranilate, methyl 4-methoxy-2-N-phenoxycarbonylanthranilate, ethyl 4-methoxy-2-N-phenoxycarbonylanthranilate, benzyl 4-methoxy-2-N-phenoxycarbonylanthranilate, methyl 4-hydroxy-2-N-phenoxycarbonylanthranilate, ethyl 4-hydroxy-2-N-phenoxycarbonylanthranilate, benzyl 4-hydroxy-2-N-phenoxycarbonylanthranilate, and the like.

The reaction for obtaining a sulfonylurea derivative represented by the formula (7) by condensing a compound represented by the formula (5) and an anthranilic acid derivative represented by the formula (6) may be performed in an aprotic solvent, for example, an ethereal solvent such as tetrahydrofuran and dioxane, a halogenic solvent such as methylene chloride, or dimethylformamide at a temperature between −50 and 50° C., preferably at a temperature between −20° C. and room temperature. As a base for use in the condensation reaction, there can be used an organic strong base such as DBU, an inorganic base such as potassium carbonate, sodium carbonate, potassium hydroxide or sodium hydroxide, or a metal base such as sodium hydride.

In the reaction of subjecting a sulfonylurea derivative represented by the formula (7) to alkali hydrolysis or hydrogenolysis to obtain a sulfonylurea derivative represented by the formula (4), a normal hydrolysis condition or a hydrogenolysis condition for esters may be used.

The above reaction may be performed by protecting the functional groups that do not participate in the reaction, and depending on the type of the protecting group, a conventional deprotection reaction such as a chemical reduction is used for deprotection. For example, when the protecting group is a t-butyl group or a t-butoxycarbonyl group, trifluoroacetic acid may be used, and when it is allyl, a palladium catalyst such as tetrakis(triphenylphosphine) palladium (0) may be used.

A compound of the formula (1) in which $R^1$ is an amino group acylated with a lower fatty acid having 1 to 4 carbons that may be substituted with a carboxylic group, an amino group acylated with an aromatic carboxylic acid that may be substituted with a carboxylic group, or an amino group acylated with a heteroaromatic carboxylic acid that may be substituted with a carboxylic group, can be obtained by acylating a compound of formula (1) in which $R^1$ represents an amino group, using a carboxylic acid, a carboxylic chloride or a carboxylic anhydride by a conventional method.

A compound of the formula (1) in which $R^1$ represents an amino group sulfonylated with a lower alkane sulfonic acid having 1 to 4 carbons that may be substituted with a carboxylic group, an amino group sulfonylated with an aromatic sulfonic acid that may be substituted with a carboxylic group, or an amino group sulfonylated with a heteroaromatic sulfonic acid that may be substituted with a carboxylic group, can be obtained by sulfonylating a compound of formula (1) in which $R^1$ represents an amino group, using a sulfonic acid, a sulfonic chloride or a sulfonic anhydride by a conventional method.

The compound obtained in the above processes may be purified by a conventional purification method such as recrystallization and column chromatography.

Also, as needed, the compound of the formula (1) obtained in the above processes may be converted to a salt by reacting it with one of various acids or bases. As an acid that can be used to convert a compound of the formula (1) to a salt, there can be mentioned an inorganic acid such as hydrochloric acid, hydrobromic acid, nitric acid, sulfuric acid and phosphoric acid, and an organic acid such as methanesulfonic acid, benzenesulfonic acid, p-toluenesulfonic acid, trifluoroacetic acid, citric acid, lactic acid, maleic acid, fumaric acid, tartaric acid, acetic acid, adipic acid, palmitic acid and tannic acid.

As a base that can be used to convert a compound of the formula (1) to a salt, there can be mentioned sodium hydroxide, lithium hydroxide, potassium hydroxide, and the like.

Some of the compounds of formula (1) contain an asymmetric center, and from the racemates of the compound one of the optical isomers may be isolated by one or more methods. For example, there can be used:

(1) a method that employs an optically active column, (2) a method that attains conversion to salts using an optically active acid or base and then performs recrystallization, (3) a method that combines the above (1) and (2), and the like.

These compounds can be evaluated for the suppressing effect of lipid deposition on the blood vessel by the method described in the Example 4 below.

When a compound claimed in the present invention is used as a preventive and/or therapeutic agent for diseases in which lipid deposition in the blood vessel is involved, a preventive or therapeutic pharmaceutical composition for diseases accompanied by abnormal vascular function, or a suppressing agent of lipid deposition in the blood vessel, one or more than one compound of the present invention, for example, may be blended and formulated into a dosage form suitable for the administration regimen according to a standard method. For example, for oral administration, a dosage form such as capsules, tablets, granules, fine granules, syrups, and dry syrups may be illustrated, and for parenteral administration, in addition to injections, suppositories, suppositories such as vaginal suppositories, nasal drugs such as sprays, ointments, and transdermal absorptive drugs such as transdermal absorptive tapes may be illustrated.

The clinical dosage of the compound of the present invention varies depending on the symptom and severity of the disease, age and the presence of complications, etc., and on the pharmaceutical formulation. In the case of oral administration, 1 to 1000 mg as an active ingredient per adult, and in the case of parenteral administration, one tenth to one half the dose of the oral administration may be administered. These doses can be increased or decreased, as appropriate, depending on the age of the patient and disease states, etc.

According to the present invention, the chymase inhibitor may be administered alone i.e. without blending with other active ingredients, but it is also possible to blend with other active ingredients and administer as pharmaceutical compositions by taking into account indicated diseases, symptoms, complications, etc. Furthermore, combined use with other active ingredients may also be possible. The amount of the above other active ingredient used is decided considering, but is not limited to, the minimum amount that exhibits effect by a single agent, development of side effects, and the like.

At the time of treatment, the selection of a pharmaceutical formulation containing the chymase inhibitor alone as active ingredient and a formulation containing it with other active ingredients may be made by a physician depending on the age and symptom of the patient, etc.

The toxicity of the compound of the present invention is low, and its acute toxicity value $LD_{50}$ against 5-week old male mice at 24 hours after oral administration is 1 g/kg or greater. The value is more than 50-times that of the expected clinical dosage, and thus it is judged that the safety of these compounds is high.

EXAMPLES

The present invention will now be described more specifically based on the Examples, and it should be noted that the scope of the present invention is not limited by these examples in any way.

Preparation Example 1

Synthesis of 7-chloro-3-(3-hydroxybenzenesulfonyl)-2,4(1H,3H)-quinazolinedione (Compound 1)

According to the synthetic method (B), 938 mg (5.42 mmol) of 3-hydroxybenzenesulfonamide was dissolved in 40 ml of tetrahydrofuran, to which 892 μl (5.96 mmol) of 1,8-diazabicyclo[5,4,0]-7-undecene (hereinafter referred to as DBU) was added dropwise. After the reaction mixture was stirred at room temperature for 15 minutes, 1.66 g (5.42 mmol) of methyl 4-chloro-2-N-phenoxycarbonylanthranilate was added and stirred overnight at room temperature. An excess water was added to the reaction mixture, which was acidified with hydrochloric acid and then extracted with ethyl acetate.

The organic layer was washed with water and saturated saline, and then dried on anhydrous magnesium sulfate and concentrated. The crude product obtained was purified by silica gel chromatography (0%–5% methanol/dichloromethane) to obtain 1.23 g (yield 59%) of methyl 4-chloro-2-{[(3-hydroxybenzenesulfonylamino)carbonyl]amino}benzoate (property: colorless amorphous, PMR (δppm, DMSO-$d_6$): 3.91 (3H, s), 7.02 (1H, m), 7.09 (1H, m), 7.34 (1H, t), 7.57 (2H, m), 7.89 (1H, d), 8.38 (1H, d), 10,94 (1H, s)). Then 1.23 g (3.2 mmol) of the sulfonylurea obtained was dissolved in 20 ml of methanol, to which 10 ml of a 2N sodium hydroxide solution was added dropwise. After the reaction mixture was stirred at room temperature for 15 minutes, an excess water was added and then it was acidified with hydrochloric acid. This was stirred and the deposited crystals were taken out by filtration and dried to obtain 992 mg of a crude carboxylic acid.

The crude product obtained was dissolved in 50 ml of tetrahydrofuran (hereinafter referred to as THF), to which 434 mg (2.68 mmol) of CDI was added and stirred on ice for 30 minutes. The reaction mixture was diluted in ethyl acetate, washed with water and saturated saline, and then dried on anhydrous magnesium sulfate and concentrated to obtain a crude product. The crude product was purified by silica gel chromatography (ethyl acetate:n-hexane=1:2) to obtain 230 mg (yield 20%: 2 steps) of the title compound. Property: colorless crystals, melting point: >200° C. (decomposition), PMR (δppm, DMSO-$d_6$): 7.12 (2H, s), 7.24 (1H, d), 7.48 (1H, t), 7.58 (2H, s), 7.85 (1H, d), 10.28 (1H, s), 11.63 (1H, s).

Preparation Example 2

Synthesis of 3-(2-aminobenzenesulfonyl)-7-chloro-2,4(1H,3H)-quinazolinedione (Compound 2)

From 2.7 g (15.7 mmol) of 2-aminobenzenesulfonamide and 4.8 g (15.7 mmol) of methyl 4-chloro-2-N-phenoxycarbonylanthranilate in a manner similar to Preparation Example 1, 3.2 g (yield 58%: 3 steps) of the title compound was obtained. Property: colorless crystals, melting point: >200° C. (decomposition), PMR (δppm, DMSO-$d_6$): 6.46 (2H, s), 6.65 (1H, t), 6.81 (1H, d), 7.12 (1H, s), 7.23 (1H, d), 7.34 (1H, t), 7.76 (1H, d), 7,86 (1H, d).

Preparation Example 3

Synthesis of 7-chloro-3-(2-methylsulfonylaminobenzenesulfonyl)-2,4(1H,3H)-quinazolinedione (Compound 3)

Twenty-two mg (0.06 mmol) of compound 2 was dissolved in 200 μl of pyridine, to which 11.6 μl (0.15 mmol) of methanesulfonyl chloride was added dropwise and stirred overnight at room temperature. Excess water was added to the reaction mixture and then extracted with ethyl acetate. The organic layer was washed with an aqueous solution of 1N hydrochloric acid and saturated saline, and then dried on anhydrous magnesium sulfate and concentrated to obtain a crude product. The crude product obtained was crystallized from diethylether to obtain 16 mg (0.04 mmol) of the title compound. Property: colorless crystals, melting point: >200° C. (decomposition), PMR (δppm, DMSO-$d_6$): 3.61 (3H, s), 7.10 (1H, d), 7.20 (1H, d), 7.74 (1H, d), 7.82–7.90 (4H, m), 8,34 (1H, d), 11.70 (1H, s).

Preparation Example 4

Synthesis of 3-(4-aminobenzenesulfonyl)-7-chloro-2,4(1H,3H)-quinazolinedione (Compound 4)

From 2.7 g (15.7 mmol) of 4-aminobenzenesulfonamide and 4.8 g (15.7 mmol) of methyl 4-chloro-2-N-phenoxycarbonylanthranilate in a manner similar to Preparation Example 1, 7.9 g (yield 94%) of methyl 2-{[(4-aminobenzenesulfonylamino)carbonyl]amino}-4-chlorobenzoate was obtained. Property: colorless amorphous, PMR (δppm, DMSO-$d_6$): 3.59 (3H, s), 5.37 (2H, s), 6.45 (2H, d), 6.83 (1H, dd), 7.41 (2H, d), 7.81 (1H, d), 8.66 (1H, d), 9.64 (1H, s).

Then from the 7.9 g (14.8 mmol) of the sulfonylurea product, 4.3 g (yield 83%: 2 steps) of the title compound was obtained in a similar manner. Property: colorless crystals, melting point: >200° C. (decomposition), PMR (δppm, DMSO-$d_6$): 6.39 (2H, s), 6.63 (2H, d), 7.09 (1H, s), 7.22 (1H, d), 7.76 (2H, d), 7.83 (1H, d), 11.51 (1H, s).

Preparation Example 5

Synthesis of 3-(3-carboxymethylbenzenesulfonyl)-7-chloro-2,4(1H,3H)-quinazolinedione (Compound 5)

After, according to the synthetic method (A), 3.27 g (11.6 mmol) of 3-allyloxycarbonylmethylbenzenesulfonyl isocyanate was dissolved in 100 ml of anhydrous THF, 1.98 g (11.5 mmol) of 4-chloroanthranilic acid was added thereto and was stirred at room temperature for 2 hours. The reaction mixture was cooled on ice water, 1.87 g (11.5 mmol) of CDI was added and the mixture was stirred on ice for 30 minutes. Excess water was added to the reaction mixture and then extracted with ethyl acetate. The organic layer was washed, dried, and concentrated to prepare a crude product, which was crystallized from a small amount of ethyl acetate to obtain 2.0 g (yield 40%) of 3-(3-allyloxycarbonylmethylbenzenesulfonyl)-7-chloro-2,4(1H,3H)-quinazolinedione.

The above allyl product obtained was dissolved in 100 ml of a formic acid-THF (1:9) mixture, to which 700 mg of triphenylphosphine was added. The reaction vessel was placed in the dark and the air in the reaction system was displaced with nitrogen, and 700 mg of tetrakis (triphenylphosphine)palladium (0) was added, and stirred overnight in the dark at room temperature. The reaction mixture was concentrated under reduced pressure, and the solid obtained was washed with methylene chloride to obtain 1.47 g (yield 81%) of the title compound. Property: colorless crystals, melting point: >200° C. (decomposition), PMR (δppm, DMSO-$d_6$): 3.76 (2H, s), 7.13 (1H, s), 7.24 (2H, d), 7.61–7.69 (2H, m), 7.86 (1H, d), 8.05 (2H, s), 12.50 (1H, br).

Preparation Example 6

Synthesis of 3-(4-carboxymethylbenzenesulfonyl)-7-chloro-2,4(1H,3H)-quinazolinedione (Compound 6)

From 1.10 g (3.95 mmol) of 4-allyloxycarbonylmethylbenzenesulfonyl isocyanate and 678 mg (3.95 mmol) of 4-chloro-anthranilic acid in a manner similar to Preparation Example 5, 657 mg (yield 38%) of 3-(4-allyloxycarbonylbenzenesulfonyl)-7-chloro-2,4(1H,3H)-quinazolinedione was obtained. From 538 mg (1.24 mmol) of this, in a similar manner, 342 mg of the title compound (yield 70%) was obtained. Property: colorless crystals, melting point: >200° C. (decomposition), PMR (δppm, DMSO-$d_6$): 3.75 (2H, s), 7.13 (1H, s), 7.23 (1H, d), 7.61–7.69 (2H, m), 7.86 (1H, d), 8.05 (2H, s), 12.07 (2H, br).

Preparation Example 7

Synthesis of (±)-2-{4-[(7-chloro-2,4(1H,3H)-quinazoline-3-yl)sulfonyl]phenyl}butyrate (Compound 7)

From 1.02 g (3.41 mmol) of tert-butyl (±)-2-(4-aminosulfonylphenyl)butyrate and 1.04 g (3.41 mmol) of methyl 4-chloro-2-N-phenoxycarbonylanthranilate in a manner similar to Preparation Example 1, 1.46 g (yield 84%) of methyl 2-[({4-[1-(t-butoxycarbonyl)propyl]benzenesulfonylamino}carbonyl)amino]-4-chlorobenzoate (property: colorless amorphous, PMR (δppm, CDCl$_3$): 0.89 (3H, t), 1.38 (9H, s), 1.69–1.76 (1H, m), 2.03–2.10 (1H, m), 3.42 (1H, t), 3.94 (3H, s), 7.04 (1H, d), 7.47 (2H, d), 7.93 (1H, d), 8.01 (2H, d), 8.45 (1H, br), 11.04 (1H, br)) was obtained. Then, 4.3 ml (8.6 mmol) of 2N sodium hydroxide was used in a similar manner to prepare 1.43 g of a carboxylic acid. Using 463 mg (2.86 mmol) of CDI, 970 mg (yield 71%: 2 steps) of (±)-2-{4-[(7-chloro-2,4(1H,3H)-quinazoline-3-yl)sulfonyl]phenyl}butyric acid t-butylester was obtained.

The butylester product obtained was dissolved in 5 ml of dichloromethane to which 5 ml of trifluoroacetic acid was added and stirred at room temperature for 40 minutes. The reaction mixture was concentrated under reduced pressure and the crude product obtained was washed with diethylether to obtain 820 mg of the title compound (yield 96%). Property: colorless crystals, melting point: >200° C. (decomposition), PMR (δppm, DMSO-$_6$): 0.84 (3H, t), 1.67–1.75 (1H, m), 1.98–2.05 (1H, m), 3.62 (1H, t), 7.11 (1H, s), 7.24 (1H, d), 7.61 (2H, d), 7,86 (1H, d), 8.13 (2H, d), 11.62 (1H, s).

Preparation Example 8

Synthesis of 3-(3-amino-4-chlorobenzenesulfonyl)-7-chloro-2,4(1H,3H)-quinazolinedione (Compound 8)

From 1.0 g (2.93 mmol) of 3-benzyloxycarbonylamino-4-chlorobenzenesulfonamide and 1.18 g (2.93 mmol) of 4-chloro-2-N-phenoxycarbonylanthranilic acid benzylester in a similar manner to Preparation Example 1, 1.43 g (yield 78%) of 2-{[(3-benzyloxycarbonylamino-4-chlorobenzenesulfonylamino)carbonyl]amino}-4-chlorobenzoic acid benzylester (property: colorless amorphous, PMR (δppm, DMSO-d$_6$): 5.19 (2H, s), 5.36 (2H, s), 7.21 (1H, dd), 7.34–7.48 (10H, m), 7.72–7.76 (2H, m), 7.97 (1H, d), 8.25 (1H, d), 8.30 (1H, d), 9.53 (1H, s), 10.30 (1H, s)) was obtained.

Among this, 1.38 g (2.20 mmol) was dissolved in 50 ml of THF, to which 200 mg of palladium-carbon (10%) was added and stirred under a hydrogen stream for 2 hours. The reaction mixture was filtered with celite to remove palladium-carbon, and the filtrate was concentrated under reduced pressure to obtain a crude product. The crude product obtained was dissolved in 50 ml of THF, to which 356 mg (2.20 mmol) of CDI on ice was added, and, in a similar manner to Preparation Example 1, 560 mg (yield 66%: 2 steps) of the title compound was obtained. Property: colorless crystals, melting point: >200° C. (decomposition), PMR (δppm, DMSO-d$_6$): 6.00 (2H, s), 7.12 (1H, s), 7.26 (2H, t), 7.48 (1H, d), 7.66 (1H, s), 7.86 (1H, d), 11.76 (1H, br).

Preparation Example 9

Synthesis of 3-(4-amino-3,5-dichlorobenzenesulfonyl)-7-chloro-2,4(1H,3H)-quinazolinedione (Compound 9)

From 1.06 g (4.40 mmol) of 4-amino-3,5-dichlorobenzenesulfonamide and 1.34 g (4.40 mmol) of methyl 4-chloro-2-N-phenoxycarbonylanthranilate in a similar manner to Preparation Example 1, 905 mg (yield 44%) of methyl 2-{[(4-amino-3,5-dichlorobenzenesulfonylamino)carbonyl]amino}-4-chlorobenzoate (property: colorless amorphous, PMR (δppm, DMSO-d$_6$): 3.87 (3H, s), 6.59 (2H, br), 7.22 (1H, dd), 7.72 (2H, s), 7.93 (1H, d), 8.24 (1H, d), 10.17 (1H, s) was obtained.

Then, from the 905 mg (2.0 mmol) of the sulfonylurea product obtained, 660 mg (yield 82%: 2 steps) of the title compound was obtained in a similar manner. Property: colorless crystals, melting point: >200° C. (decomposition), PMR (δppm, DMSO-d$_6$): 6.80 (2H, s), 7.12 (1H, s), 7.24 (1H, d), 7.86 (1H, d), 7.92 (2H, s), 11.63 (1H, br).

Preparation Example 10

Synthesis of 3-(3-amino-4-methylbenzenesulfonyl)-7-chloro-2,4(1H,3H)-quinazolinedione (Compound 10)

From 960 mg (3.00 mmol) of 3-benzyloxycarbonylamino-4-methylbenzenesulfonamide and 1.14 g (3.00 mmol) of 4-chloro-2-N-phenoxycarbonylanthranilic acid benzylester in a similar manner to Preparation Example 8, 1.14 g (yield 62%) of 2-{[(3-benzyloxycarbonylamino-4-methylbenzenesulfonylamino)carbonyl]amino}-4-chlorobenzoic acid benzylester (property: colorless amorphous, PMR (δppm, DMSO-d$_6$): 2.30 (3H, s), 5.17 (2H, s), 5.36 (2H, s), 7.20 (1H, dd), 7.33–7.48 (11H, m), 7.63 (1H, d), 7.97 (1H, d), 8.11 (1H, s), 8.25 (1H, s), 9.27 (1H, s), 10.30 (1H, s), 12.20 (1H, br)) was obtained.

Then, from the 1.14 g (1.87 mmol) of the sulfonylurea product obtained, 190 mg (yield 27%: 2 steps) of the title compound was obtained in a similar manner. Property: colorless crystals, melting point: >200° C. (decomposition), PMR (δppm, DMSO-d$_6$): 2.12 (3H, s), 5.47 (2H, s), 7.12 (1H, s), 7.16–7.25 (3H, m), 7.38 (1H, s), 7.85 (1H, d), 11.58 (1H, s).

Preparation Example 11

Synthesis of 3-[(3-carboxymethylaminophenyl)sulfonyl]-7-chloro-2,4(1H,3H)-quinazolinedione (Compound 11)

From 1.62 g (5.65 mmol) of 3-t-butoxycarbonylmethylaminobenzenesulfonamide and 1.73 g (5.65 mmol) of methyl 4-chloro-2-N-phenoxycarbonylanthranilate in a similar manner to Preparation Example 7, 209 mg (yield 9%: 4 steps) of the title compound was obtained. Property: colorless crystals, melting point: >200° C. (decomposition), PMR (δppm, DMSO-d$_6$): 3.86 (2H, s), 6.88 (1H, s), 7.12 (1H, s), 7.24 (1H, d), 7.30–7.38 (3H, m), 7.86 (1H, d), 11.61 (1H, br).

Preparation Example 12

Synthesis of 3-(3-aminobenzenesulfonyl)-7-chloro-2,4(1H,3H)-quinazolinedione (Compound 12)

From 3.5 g (12.9 mmol) of 3-t-butoxycarbonylaminobenzenesulfonamide and 3.9 g (12.8 mmol) of methyl 4-chloro-2-N-phenoxycarbonylanthranilate in a similar manner to Preparation Example 7, 2.2 g (yield 49%: 4 steps) of the title compound was obtained. Property: colorless crystals, melting point: >200° C. (decomposition), PMR (δppm, DMSO-d$_6$): 5.72 (2H, s), 6.87 (1H, d), 7.12 (1H, s), 7.23–7.27 (2H, m), 7.33 (1H, s), 7.86 (1H, d), 11.61 (1H, s).

Preparation Example 13

Synthesis of 2-{3-[(7-chloro-2,4(1H,3H)-quinazolinedione-3-yl)sulfonyl]phenylaminocarbonyl}propionic acid (Compound 13)

One hundred mg (0.28 mmol) of compound 12 was dissolved in 5 ml of THF, to which 100 mg (1.0 mmol) of succinic anhydride was added and heated to reflux for 3 hours. The reaction mixture was concentrated under reduced pressure, and the crude product obtained was crystallized from ethyl acetate-diethylether to obtain 120 mg (yield 96%) of the title compound. Property: colorless crystals, melting point: 187–188° C., PMR (δppm, DMSO-d$_6$): 2.54 (2H, d), 2.59 (2H, d), 7.12 (1H, s), 7.24 (1H, d), 7.59 (1H, t), 7.80 (1H, d), 7.86 (1H, d), 7.96 (1H, d), 8.41 (1H, s), 10.40 (1H, s), 11.63 (1H, br), 12.10 (1H, br).

Preparation Example 14

Synthesis of 3-{3-[(7-chloro-2,4(1H,3H)-quinazolinedione-3-yl)sulfonyl]phenyl}acrylic acid (Compound 14)

From 1.54 g (5.44 mmol) of 3-(3-aminosulfonyl)phenylacrylic acid t-butylester and 1.66 g (5.44 mmol) of methyl 4-chloro-2-N-phenoxycarbonylanthranilate in a similar manner to Preparation Example 7, 2.18 g (yield 81%) of methyl 2-({[3-{3-t-butoxy-3-oxo-1-propenyl}benzenesulfonylamino]carbonyl}amino)-4-chlorobenzoate (property: colorless amorphous, PMR (δppm, CDCl$_3$): 1.53 (9H, s), 3.95 (3H, s), 6.46 (1H, d), 7.05 (1H, d), 7.55 (1H, m), 7.57 (1H, d), 7.72 (1H, m), 7.93 (1H, m), 8.04 (1H, m), 8.27 (1H, s), 8.46 (1H, d), 11.05 (1H, br)) was obtained.

Then, from the 2.18 g (4.4 mmol) of the sulfonylurea product obtained, 698 mg (yield 37%: 3 steps) of the title compound was obtained in a similar manner. Property: colorless crystals, melting point: >200° C. (decomposition), PMR (δppm, DMSO-d$_6$): 6.65 (1H, d), 7.12 (1H, s), 7.25 (1H, d), 7.69 (1H, d), 7.72 (1H, t), 7.87 (1H, d), 8.12 (2H, q), 8.37 (1H, s), 11.64 (1H, s).

Preparation Example 15

Synthesis of 4-[(7-chloro-2,4(1H,3H)-quinazolinedione-3-yl)sulfonyl]salicylic acid (Compound 15)

From 1.0 g (3.66 mmol) of 4-t-butoxycarbonyl-3-hydroxybenzenesulfonamide and 1.12 g (3.66 mmol) of methyl 4-chloro-2-N-phenoxycarbonylanthranilate in a similar manner to Preparation Example 7, 1.79 g (yield 100%) of methyl 2-{[(4-t-butoxycarbonyl-3-hydroxybenzenesulfonylamino)carbonyl]amino}-4-chlorobenzoate (property: colorless amorphous, PMR (δppm, DMSO-d$_6$): 1.57 (9H, s), 3.87 (3H, s), 7.14 (1H, d), 7.40–7.45 (2H, m), 7.85 (1H, d), 7.92 (1H, d), 8.32 (1H, d), 10.13 (1H, s), 10.82 (1H, s)) was obtained.

Then, from the 1.78 g (3.66 mmol) of the sulfonylurea product obtained, 370 mg (yield 25%: 3 steps) of the title compound was obtained in a similar manner. Property: colorless crystals, melting point: >200° C. (decomposition), PMR (δppm, DMSO-d$_6$): 7.13 (1H, s), 7.26 (1H, d), 7.69 (1H, d), 7.87 (1H, d), 8.01 (1H, d), 11.67 (1H, s).

Preparation Example 16

Synthesis of 4-[(7-chloro-2,4(1H,3H)-quinazolinedione-3-yl)sulfonyl]salicylic acid monosodium salt (Compound 16)

Fifty mg (0.13 mmol) of compound 15 was suspended in about 1 ml of THF, to which 126 μl of 1N sodium hydroxide in water was added dropwise. After confirming that the solution became homogeneous, 30 ml of water was added and lyophilized to obtain 52 mg of the amorphous title compound on a quantitative basis. Property: colorless amorphous, PMR (δppm, CD$_3$OD): 7.11 (1H, s), 7.19 (1H, d), 7.58 (1H, d), 7.63 (1H, s), 7.92 (1H, d), 8.03 (1H, d).

Preparation Example 17

Synthesis of 4-[(7-chloro-2,4(1H,3H)-quinazolinedione-3-yl)sulfonyl]anthranilic acid (Compound 17)

From 2.84 g (6.99 mmol) of 3-benzyloxycarbonylamino-4-t-butoxycarbonylbenzenesulfonamide and 2.67 g (6.99 mmol) of 4-chloro-2-N-phenoxycarbonylanthranilic acid benzylester in a similar manner to Preparation Example 8, 3.74 g (yield 77%) of 2-{[(3-benzyloxycarbonylamino-4-t-butoxycarbonylbenzenesulfonylamino)carbonyl]amino}-4-chlorobenzoic acid benzylester (property: colorless amorphous, PMR (δppm, DMSO-d$_6$): 1.54 (9H, s), 5.19 (2H, s), 5.34 (2H, s), 7.05 (1H, m), 7.34–7.58 (10H, m), 7.60 (1H, d), 7.90 (1H, d), 7.98 (1H, d), 8.50 (1H, br), 8.62 (1H, s), 10.00 (1H, br), 10.41 (1H, s)) was obtained.

Then, from the 3.74 g (5.39 mmol) of the sulfonylurea product obtained, 690 mg (yield 30%: 2 steps) of 4-[(7-chloro-2,4(1H,3H)-quinazolinedion-3-yl)sulfonyl] anthranilic acid t-butylester was obtained in a similar manner, which was subjected to a similar debutylation reaction to obtain 503 mg (yield 84%) of the title compound. Property: colorless crystals, melting point: >200° C. (decomposition), PMR (δppm, DMSO-d$_6$): 7.14 (1H, s), 7.18 (1H, d), 7.25 (1H, d), 7.59 (1H, s), 7,87 (1H, d), 7.89 (1H, d), 11.62 (1H, s).

Preparation Example 18

Synthesis of 4-[(7-chloro-2,4(1H,3H)-quinazolinedione-3-yl)sulfonyl]anthranilic acid monosodium salt (Compound 18)

Fifty mg (0.13 mmol) of compound 17 was suspended in about 1 ml of THF, to which 126 μl of 1N sodium hydroxide in water was added dropwise. After confirming that the solution became homogeneous, 30 ml of water was added and lyophilized to obtain 52 mg of the amorphous title compound on a quantitative basis. Property: colorless amorphous, PMR (δppm, DMSO-d$_6$): 7.11–7.22 (3H, m), 7.37 (1H, s), 7.83 (1H, d), 7.91 (1H, d).

Preparation Example 19

Synthesis of 3-(4-hydroxybenzenesulfonyl)-7-chloro-2,4(1H,3H)-quinazolinedione (Compound 19)

From 1.50 g (7.03 mmol) of 4-allyloxybenzenesulfonyl isocyanate and 1.2 g (7.03 mmol) of 4-chloroanthranilic acid in a similar manner to Preparation Example 5, 1.5 g (yield 53%) of 3-(4-allyloxybenzenesulfonyl)-7-chloro-2,4(1H,3H)-quinazolinedione was obtained. From 500 mg (1.27 mmol) among this, 405 mg of the title compound (yield 90%) was obtained in a similar manner. Property: colorless crystals, melting point: >200° C. (decomposition), PMR (δppm, DMSO-d$_6$): 6.98 (2H, d), 7.11 (1H, s), 7.23 (1H, d), 7.85 (1H, d), 8.00 (2H, d), 11.25 (1H, br).

Preparation Example 20

Synthesis of 4-[(2,4(1H,3H)-quinazolinedione-3-yl)sulfonyl]salicylic acid (Compound 20)

From 618 mg (2.26 mmol) of 4-t-butoxycarbonyl-3-hydroxybenzenesulfonamide and 613 mg (2.26 mmol) of 2-N-phenoxycarbonylanthranilic acid methylester in a similar manner to Preparation Example 17, 792 mg (yield 78%) of methyl 2-{[(4-t-butoxycarbonyl-3-hydroxybenzenesulfonylamino)carbonyl]amino}benzoate (property: colorless amorphous, PMR (δppm, CDCl$_3$): 1.60 (9H, s), 3.97 (3H, s), 7.09 (1H, t), 7.49–7.52 (2H, m), 7.65 (1H, d), 7.90 (1H, d), 8.01 (1H, dd), 8.33 (1H, d), 10.98 (1H, s), 11.18 (1H, s)) was obtained.

Then, from the 790 mg (1.75 mmol) of the sulfonylurea product obtained, 100 mg (yield 8%: 3 steps) of the title compound was obtained in a similar manner. Property: colorless crystals, melting point: >200° C. (decomposition), PMR (δppm, DMSO-d$_6$): 7.13 (1H, d), 7.22 (1H, t), 7.63–7.69 (3H, m), 7.87 (1H, d), 8.01 (1H, d), 11.57 (1H, s).

Preparation Example 21

Synthesis of 5-[(7-chloro-2,4(1H,3H)-quinazolinedione-3-yl)sulfonyl]salicylic acid (Compound 21)

From 320 mg (1.17 mmol) of 3-t-butoxycarbonyl-4-hydroxybenzenesulfonamide and 447 mg (1.17 mmol) of 4-chloro-2-N-phenoxycarbonylanthranilic acid benzylester in a similar manner to Preparation Example 17, 611 mg (yield 93%) of 2-{[(3-t-butoxycarbonyl-4-hydroxybenzenesulfonylamino)carbonyl]amino}-4-chlorobenzoic acid benzylester (property: colorless amorphous, PMR (δppm, CDCl$_3$): 1.62 (9H, s), 5.35 (2H, s), 7.01–7.05 (2H, m), 7.37–7.41 (5H, m), 7.96 (1H, d), 8.10 (1H, dd), 8.46–8.48 (2H, m), 10.99 (1H, s), 11.66 (1H, s)) was obtained.

Then, from the 611 mg (1.09 mmol) of the sulfonylurea product obtained, 114 mg (yield 33%: 3 steps) of the title compound was obtained in a similar manner. Property: colorless crystals, melting point: >200° C. (decomposition), PMR (δppm, DMSO-d$_6$): 7.11 (1H, s), 7.19 (1H, d), 7.24 (1H, d), 7.86 (1H, d), 8.20 (1H, d), 8.56 (1H, s), 11.57 (1H, s).

Preparation Example 22

Synthesis of 3-(3-acetamide-4-methoxybenzenesulfonyl)-7-chloro-2,4(1H,3H)-quinazolinedione (Compound 22)

From 500 mg (2.19 mmol) of 3-acetamide-4-methoxybenzenesulfonamide and 836 mg (2.19 mmol) of 4-chloro-2-N-phenoxycarbonylanthranilic acid benzylester in a similar manner Preparation Example 8, 812 mg (yield 70%) of 2-{[(3-acetylamino-4-methoxybenzenesulfonylamino)carbonyl]amino}-4-chlorobenzoic acid benzylester (property: colorless amorphous, PMR (δppm, DMSO-d$_6$): 2.12 (3H, s), 3.93. (3H, s), 5.36 (2H, s), 7.20 (1H, d), 7.24 (1H, d), 7.36–7.48 (5H, m), 7.69 (1H, d), 7.96 (1H, d), 8.24 (1H, d), 8.67 (1H, s), 9.39 (1H, s), 10.25 (1H, s), 12.11 (1H, br)) was obtained.

Then, from the 611 mg (1.09 mmol) of the sulfonylurea product obtained, 250 mg (yield 39%: 2 steps) of the title compound was obtained in a similar manner. Property: colorless crystals, melting point: >200° C. (decomposition), PMR (δppm, DMSO-d$_6$): 2.12 (3H, s), 3.95 (3H, s), 7.12 (1H, s), 7.23 (1H, d), 7.30 (1H, d), 7.85 (1H, d), 7.89 (1H, d), 8.80 (1H, s), 9.42 (1H, s), 11.59 (1H, br)).

Preparation Example 23

Synthesis of 3-(3-amino-4-methoxybenzenesulfonyl)-7-chloro-2,4(1H,3H)-quinazolinedione (Compound 23)

From 400 mg (1.40 mmol) of 3-t-butoxycarbonylamino-4-methoxybenzenesulfonamide and 533 mg (1.40 mmol) of 4-chloro-2-N-phenoxycarbonylanthranilic acid benzylester in a similar manner to Preparation Example 17, 86 mg (yield 16%: 4 steps) of the title compound was obtained. Property: colorless crystals, melting point: >200° C. (decomposition), PMR (δppm, DMSO-d$_6$): 3.81 (3H, s), 7.26–7.37 (5H, m), 7.77 (1H, s), 7.90 (1H, d), 7.94 (1H, d), 11.73 (1H, s)

Preparation Example 24

Synthesis of 7-chloro-3-(4-methoxy-3-methylsulfonylaminobenzenesulfonyl)-2,4(1H,3H)-quinazolinedione (Compound 24)

From 500 mg (1.89 mmol) of 4-methoxy-3-methylsulfonylaminobenzenesulfonamide and 722 mg (1.89 mmol) of 4-chloro-2-N-phenoxycarbonylanthranilic acid benzylester in a similar manner to Preparation Example 8, 888 mg (yield 83%) of 2-({[(4-methoxy-3-methylsulfonylamino)benzenesulfonylamino]carbonyl}amino)-4-chlorobenzoic acid benzylester (property: colorless amorphous, PMR (δppm, DMSO-d$_6$): 2.12 (3H, s), 3.93 (3H, s), 5.36 (2H, s), 7.20 (1H, d), 7.24 (1H, d), 7.36–7.48 (5H, m), 7.69 (1H, d), 7.96 (1H, d), 8.24 (1H, s), 8.67 (1H, s), 9.39 (1H, s), 10.25 (1H, s), 12.11 (1H, br)) was obtained.

Then, from the 880 mg (1.55 mmol) of the sulfonylurea product obtained, 620 mg (yield 85%: 2 steps) of the title compound was obtained in a similar manner. Property: colorless crystals, melting point: >200° C. (decomposition), PMR (δppm, DMSO-d$_6$): 3.04 (3H, s), 3.94 (3H, s), 7.11 (1H, s), 7.23 (1H, d), 7.34 (1H, d), 7.86 (1H, d), 7.99 (1H, d), 8.10 (1H, s)).

Preparation Example 25

Synthesis of 4-[(7-chloro-2,4(1H,3H)-quinazolinedione-3-yl)sulfonyl]-1-hydroxy-2-naphthylic acid (Compound 25)

From 323 mg (1.00 mmol) of 3-t-butoxycarbonyl-4-hydroxy-1-naphthalenesulfonamide and 381 mg (1.00 mmol) of 4-chloro-2-N-phenoxycarbonylanthranilic acid benzylester in a similar manner to Preparation Example 17, 447 mg (yield 73%) of 4-({[(2-benzyloxycarbonyl-5-chloroanilino)carbonyl]amino}sulfonyl)-1-hydroxy-2-naphthalene carboxylic acid t-butylester (property: colorless amorphous, PMR (δppm, DMSO-d$_6$): 1.66 (9H, s), 5.34 (3H, s), 6.98 (1H, d), 7.35–7.48 (5H, m), 7.66 (1H, m), 7.81 (1H, m), 7.89 (1H, d), 8.37 (2H, m), 8.44 (1H, s), 8.71 (1H, d), 10.02 (1H, br), 12.52 (1H, br)) was obtained.

Then, from the 445 mg (0.72 mmol) of the sulfonylurea product obtained, 56 mg (yield 18%: 3 steps) of the title compound was obtained in a similar manner. Property: colorless crystals, melting point: >200° C. (decomposition), PMR (δppm, DMSO-d$_6$): 7.08 (1H, s), 7.20 (1H, d), 7.63 (1H, t), 7.77 (1H, t), 7.84 (1H, d), 8.42 (1, d), 8.51 (1H, d), 8.75 (1H, s), 11.57 (1H, s).

Preparation Example 26

Synthesis of 5-[(7-chloro-2,4(1H,3H)-quinazolinedione-3-yl)sulfonyl]anthranilic acid (Compound 26)

From 834 mg (2.05 mmol) of 4-benzyloxycarbonylamino-3-t-butoxycarbonylbenzenesulfonamide and 783 mg (2.05 mmol) of 4-chloro-2-N-phenoxycarbonylanthranilic acid benzylester in a similar manner to Preparation Example 17, 1.18 g (yield 83%) of 2-{[(4-benzyloxycarbonylamino-3-t-butoxycarbonylbenzenesulfonylamino)carbonyl]amino}-4-chlorobenzoic acid benzylester (property: colorless amorphous, PMR (δppm, CDCl$_3$): 1.56 (9H, s), 5.22 (2H, s), 5.37 (2H, s), 7.04 (1H, dd), 7.33–7.42 (10H, m), 7.97 (1H, d), 8.14 (1H, d), 8.45 (1H, d), 8.60 (1H, d), 8.65 (1H, d), 11.01 (1H, s), 11.11 (1H, s)) was obtained.

Then, from the 1.17 g (1.69 mmol) of the sulfonylurea product obtained, 404 mg (yield 60%: 3 steps) of the title compound was obtained in a similar manner. Property: colorless crystals, melting point: >200° C. (decomposition), PMR (δppm, DMSO-d$_6$): 6.89 (1H, d), 7.11 (1H, s), 7.23 (1H, d), 7.85 (1H, d), 7.98 (1H, d), 8.51 (1H, s), 11.51 (1H, s).

Preparation Example 27

Synthesis of 4-[(7-methoxy-2,4(1H,3H)-quinazolinedione-3-yl)sulfonyl]anthranilic acid (Compound 27)

From 500 mg (1.23 mmol) of 3-benzyloxycarbonylamino-4-t- butoxycarbonylbenzenesulfonamide and 460 mg (1.22 mmol) of 4-methoxy-2-N-phenoxycarbonylanthranilic acid benzylester in a similar manner to Preparation Example 17, 15 mg (yield 3.1%: 4 steps) of the title compound was obtained. Property: colorless crystals, melting point: >200° C. (decomposition), PMR (δppm, DMSO-$d_6$): 3.82 (3H, s), 6.58 (1H, s), 6.80 (1H, d), 7.16 (1H, d), 7.56 (1H, s), 7.80 (1H, d), 7.90 (1H, d), 11.49 (1H, s).

Preparation Example 28

Synthesis of (±)-7-[(7-chloro-2,4(1H,3H)-quinazolinedione-3-yl)sulfonyl]-2-oxo-1H,3H-quinoline-3-carboxylic acid (Compound 28)

From 400 mg (1.23 mmol) of (±)-3-t-butoxycarbonyl-2-oxo-1H,3H-quinoline-7-sulfonamide and 468 mg (1.23 mmol) of 4-chloro-2-N-phenoxycarbonylanthranilic acid benzylester in a similar manner to Preparation Example 17, 649 mg (yield 86%) of 8-({[(2-benzyloxycarbonyl-5-chloroanilino)carbonyl]amino}sulfonyl)-2-oxo-1,2,3,4-tetrahydro-3-quinolinecarboxylic acid t-butylester (property: colorless amorphous, PMR (δppm, $CDCl_3$): 1.32 (9H, s), 3.18–3.30 (2H, m), 3.54 (1H, m), 5.35 (2H, s), 6.85 (1H, m), 7.00 (1H, m), 7.35–7.39 (5H, m), 7.87–7.96 (3H, m), 8.47 (1H, m), 8.78 (1H, br), 10.92 (1H, br)) was obtained.

Then, from the 640 mg (1.04 mmol) of the sulfonylurea product obtained, 258 mg (yield 55%: 3 steps) of the title compound was obtained in a similar manner. Property: colorless crystals, melting point: >200° C. (decomposition), PMR (δppm, DMSO-$d_6$): 3.23–3.31 (2H, m), 3.59 (1H, t), 7.07 (1H, d), 7.12 (1H, s), 7.25 (1H, d), 7.86 (1H, d), 7.96 (1H, d), 7.98 (1H, d), 10.84 (1H, s), 11.60 (1H, s).

Preparation Example 29

Synthesis of (±)-6-[(7-chloro-2,4(1H,3H)-quinazolinedione-3-yl)sulfonyl]-3-oxo-1,4-benzoxadine-2-carboxylic acid (Compound 29)

From 300 mg (0.91 nmol) of (±)-2-t-butoxycarbonyl-3-oxo-1,4-benzoxadine-6-sulfonamide and 349 mg (0.91 mmol) of 4-chloro-2-N-phenoxycarbonylanthranilic acid benzylester in a similar manner to Preparation Example 17, 417 mg (yield 74%) of 5-({[(2-benzyloxycarbonyl-5-chloroanilino)carbonyl]amino}sulfonyl)-3-oxo-3,4-dihydro-2H-1,4-benzoxadine-2-carboxylic acid t-butylester (property: colorless amorphous, PMR (δppm, DMSO-$d_6$): 1.29 (9H, s), 5.37 (2H, s), 5.42 (2H, s), 7.19–7.26 (2H, m), 7.37–7.57 (7H, m), 7.97 (1H, d), 8.25 (1H, d), 10.27 (1H, s), 11.25 (1H, s), 12.22 (1H, br)) was obtained.

Then, from the 417 mg (0.68 mmol) of the sulfonylurea product obtained, 100 mg (yield 32%: 3 steps) of the title compound was obtained in a similar manner. Property: colorless crystals, melting point: >200° C. (decomposition), PMR (δppm, DMSO-$d_6$): 5.47 (1H, s), 7.11 (1H, s), 7.24 (1H, d), 7.29 (1H, d), 7.76 (1H, s), 7.78 (1H, d), 7.86 (1H, d), 11.25 (1H, s), 11.62 (1H, s).

Preparation Example 30

Synthesis of 4-[(7-hydroxy-2,4(1H,3H)-quinazolinedione-3-yl)sulfonyl]anthranilic acid (Compound 30)

From 620 mg (1.53 mmol) of 3-benzyloxycarbonylamino-4-t-butoxycarbonylbenzenesulfonamide and 550 mg (1.51 mmol) of 4-hydroxy-2-N-phenoxycarbonylanthranilic acid benzylester in a similar manner to Preparation Example 17, 25 mg (yield 4%: 4 steps) of the title compound was obtained. Property: colorless crystals, melting point: >200° C. (decomposition), PMR (δppm, DMSO-$d_6$): 6.48 (1H, s), 6.61 (1H, d), 7.14 (1H, d), 7.51 (1H, s), 7.70 (1H, d), 7.90 (1H, d), 10.80 (1H, s), 11.39 (1H, s).

Preparation Example 31

Synthesis of 4-[(7-chloro-2,4(1H,3H)-quinazolinedione-3-yl)sulfonyl]-2-N-propionylanthranilic acid (Compound 31)

Eight hundred and forty mg (1.86 mmol) of compound 17 was dissolved in 8 ml of 1,4-dioxane, to which 240 μl (2.79 mmol) of propionyl chloride was added dropwise and stirred overnight at 60° C. Excess water was added to the reaction mixture and then extracted with ethyl acetate. The organic layer was washed, dried, and concentrated to obtain the crude product of 4-[(7-chloro-2,4(1H,3H)-quinazolinedione-3-yl)sulfonyl]-2-N-propionylanthranilic acid t-butylester. After the crude product obtained was stirred in 3 ml of trifluoroacetic acid at room temperature for 1 hour, the reaction mixture was concentrated under reduced pressure to obtain a crude product, which was washed with diethylether to obtain 400 mg (yield 48%: 2 steps) of the title compound. Property: colorless crystals, melting point: >200° C. (decomposition), PMR (δppm, DMSO-$d_6$): 1.10 (3H, t), 2.45 (2H, dd), 7.11 (1H, s), 7.24 (1H, d), 7.85 (1H, d), 7.88 (1H, d), 8.17 (1H, d), 9.18 (1H, s), 11.07 (1H, s), 11.63 (1H, s).

Preparation Example 32

Synthesis of 4-[(6-chloro-2,4(1H,3H)-quinazolinedione-3-yl)sulfonyl]anthranilic acid (Compound 32)

From 300 mg (0.74 mmol) of 3-benzyloxycarbonylamino-4-t-butoxycarbonylbenzenesulfonamide and 310 mg (0.81 mmol) of 5-chloro-2-N-phenoxycarbonylanthranilic acid benzylester in a similar manner to Preparation Example 17, 75 mg (yield 26%: 4 steps) of the title compound was obtained. Property: colorless crystals, melting point: >200° C. (decomposition), PMR (δppm, DMSO-$d_6$): 7.13–7.20 (2H, m), 7.56 (1H, s), 7.72 (1H, d), 7.82 (1H, s), 7.90 (1H, d), 11.68 (1H, s).

Preparation Example 33

Synthesis of 4-[(7-chloro-2,4(1H,3H)-quinazolinedione-3-yl)sulfonyl]-2-N-methanesulfonylanthranilic acid (Compound 33)

From 200 mg (0.44 mmol) of compound 17 in a similar manner to Preparation Example 3, 81 mg of 4-[(7-chloro-2,4(1H,3H)-quinazolinedione-3-yl)sulfonyl]-2-N-methanesulfonylanthranilic acid t-butylester was obtained, which was similarly subjected to a debutylation reaction to obtain 53 mg (yield 25%: 2 steps) of the title compound. Property: colorless crystals, melting point: >200° C. (decomposition), PMR (δppm, DMSO-$d_6$): 3.24 (3H, s), 7.11 (1H, s), 7.25 (1H, d), 7.85–7.91 (2H, m), 8.23 (1H, d), 8.39 (1H, s), 11.05 (1H, br), 11.70 (1H, s).

Preparation Example 34

Synthesis of 3-(3-aminobenzenesulfonyl)-7-chloro-2,4(1H,3H)quinazolinedione methanesulfonic acid salt (Compound 34)

2.15 g (6.10 mmol) of compound 12 was dissolved in 65 ml of THF, to which 0.4 ml of methanesulfonic acid was added. To this solution was added 200 ml of ether, and a precipitate that deposited was filtered to obtain 2.59 g (yield 95%) of the title compound. Property: colorless amorphous, PMR (δppm, DMSO-d$_6$): 2.35 (3H, s), 6.98 (1H, d), 7.12 (1H, m), 7.25 (1H, m), 7.34 (2H, s), 7.43 (1H, m), 7.86 (1H, s), 11.64 (1H, s).

Example 1

Evaluation of Inhibitory Activity of Test Compounds to Human Chymase

Human heart chymase was purified according to the method of Urata et al. (J. Biol. Chem. 265: 22348, 1990). The inhibitory activity of the compound of the present invention was determined as follows. Purified enzyme was diluted with 0.1 M Tris-HCl buffer (pH 7.5) containing 1 M sodium chloride and 0.01% Triton X-100 to appropriate concentrations. Suc-Ala-Ala-Pro-Phe-MCA (Peptide Institute Inc.) was dissolved in 10 mM dimethyl sulfoxide (hereinafter referred to as DMSO) and diluted 20-fold with 0.1 M Tris-HCl buffer (pH 7.5) containing 1 M sodium chloride and 0.01% Triton X-100 to an appropriate concentration to prepare substrate solution.

5 μl of the test sample in DMSO was added to 75 μl of the enzyme solution and preincubated at 30° C. for 10 minutes. Then, 20 μl of the substrate solution was added to the test sample-enzyme mixture, and incubated at 30° C. Ten minutes later, 50 μl of 30% acetic acid was added to stop the enzymatic reaction, and the amount of AMC formed was determined using a fluorophotometer. At the same time, 5 μl of DMSO in stead of the test sample was added and reacted simultaneously as a control. The inhibitory activity to human chymase was calculated based on the value of the control, and then the inhibition percentage and the 50% inhibition concentration (IC$_{50}$) were determined.

The IC50 values of representative compounds are shown in Table 1.

TABLE 1

| Preparation Example No. | IC$_{50}$ value (μM) | t$_{1/2}$ (min) |
| --- | --- | --- |
| 1 | 0.36 | 78 |
| 2 | 0.14 | 175 |
| 8 | 0.035 | 29 |
| 10 | 0.17 | 167 |
| 12 | 0.44 | 249 |
| 13 | 0.3 | 97 |
| 16 | 0.84 | >240 |
| 17 | 0.14 | 260 |
| 18 | 0.14 | 103 |
| 21 | 0.34 | — |
| 22 | 0.3 | 104 |
| 24 | 0.32 | 79 |
| 27 | 4.0 | 263 |
| 29 | 1.7 | >240 |
| 32 | 1.5 | 74 |
| 34 | 0.36 | 709 |

Example 2

Stability in Human Plasma

2 μl of 1 mM test sample in DMSO was added to 198 μl of 50% of human plasma solution in a 50 mM sodium phosphate buffer (pH 7.2) and incubated at 30° C. At 0, 5, and 15 minutes, 800 μl of acetonitrile was added to the test sample-plasma mixture, which was mixed and deproteinized. The supernatant obtained by centrifugation (12,000 rpm, one minute) was diluted with the same volume of distilled water, and the intact compound in the solution was determined by HPLC analysis.

The half life (t$_{1/2}$) of the test sample in the plasma solution was calculated from the recovery at each time point using an exponential regression analysis. The plasma half life (t$_{1/2}$) for representative compounds is shown in Table 1.

Example 3

Aorta Lipid Deposition Model in Hamster

An aorta lipid deposition model was induced by a high-cholesterol diet. A high-cholesterol diet was prepared by adding 0.5% cholesterol and 10% coconut oil (KBT Oriental Co.) to a standard rodent feed containing 5.1% fat and 0.07% cholesterol (KBT oriental Co.). 8-week-old male Golden Syrian hamsters (KBT Oriental Co.) (100–130 g) were given the high-cholesterol diet for 12 weeks to induce lipid deposition in the aorta. A group to which a standard rodent feed was given for 12 weeks was used as the control.

On week 12 after the start of the high-cholesterol diet, total cholesterol, low density lipoprotein (LDL) cholesterol, and high density lipoprotein (HDL) cholesterol levels in the peripheral blood and chymase-like activity in the aorta was determined. Chymase-like activity was measured using Ang I as the substrate, and expressed by subtracting the activity inhibited by aprotinin from the activity inhibited by chymostatin (M. Akasu, et al., Hypertension 32: 514–20, 1998, M. Ihara, et al., Hypertension 33: 1399–405, 1999).

Lipid deposition in the aorta was evaluated by harvesting the aorta on week 12 after the start of the high-cholesterol diet and performing a histopathological analysis. Namely, the ascending aorta from its junction with the heart to the middle part was removed, washed in an ice-cold saline, and then 3–5 mm segments containing the aortic cusp region were cryopreserved in Tissue-Tek O.C.T. Compound (Miles Inc.). Then, the frozen sections of 6 μm were prepared, fixed in 10% formalin for 10 minutes, washed with distilled water, and stained with the Oil red O welding (Muto Pure Chemicals) at 60° C. for 5 minutes.

Figure 1:
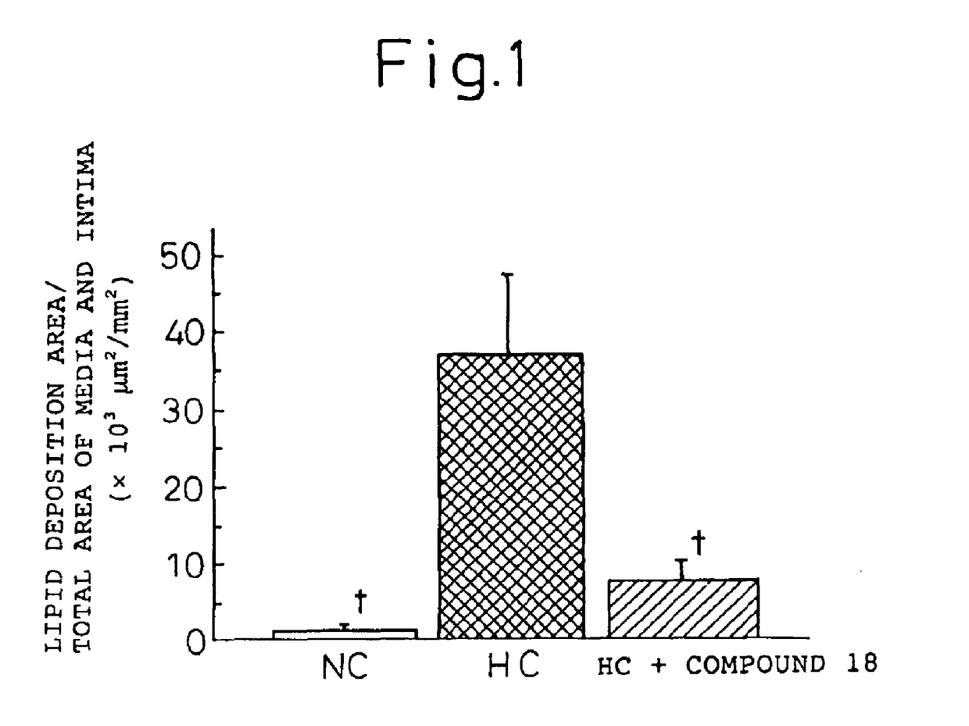
FIG. 1 is a graph showing that arterial lipid deposition was increased in the hamsters that received a high-cholesterol diet (HC) as compared to the hamsters that received a normal diet (NC), and that the lipid deposition was decreased by the administration of chymase inhibitor (HC+compound 18 of the present invention).

Then, the sections were washed with 60% isopropanol and distilled water, and counterstained with hematoxylin for 2 minutes. After washing with 1/4 saturated LiCO3, lipid deposition was evaluated by microscopic observation. Also, the area of the lipid deposition region (the region stained to an orange color with Oil red O) was quantitated on the histological pictures by NIH Image software ver. 1.61.
Result:

In the aorta of high cholesterol diet-treated hamster, a conspicuous lipid deposition was observed in the intimal region. In this model (n=6) as compared to the control group (n=6), a marked increase in the lipid deposition area in the aortic cusp region was observed (FIG. 1).

Also, there was a significant increase in plasma levels of total cholesterol, LDL cholesterol and HDL cholesterol in this model as compared to the control group (their respective values were 4.16±0.36 vs. 12.59±1.01 mmol/L, 1.15±0.26 vs. 5.48±0.67 mmol/L and 1.86±0.08 vs. 3.62±0.10 mmol/L, n=6 each, p<0.01).

Furthermore, there was a significant increase in the chymase-like activity in the aorta in this model as compared to the control group (19.2±2.6 vs. 9.3±1.2 nmol/min/g wet tissue, respectively, n=6 each, p<0.01).

Figure 2:
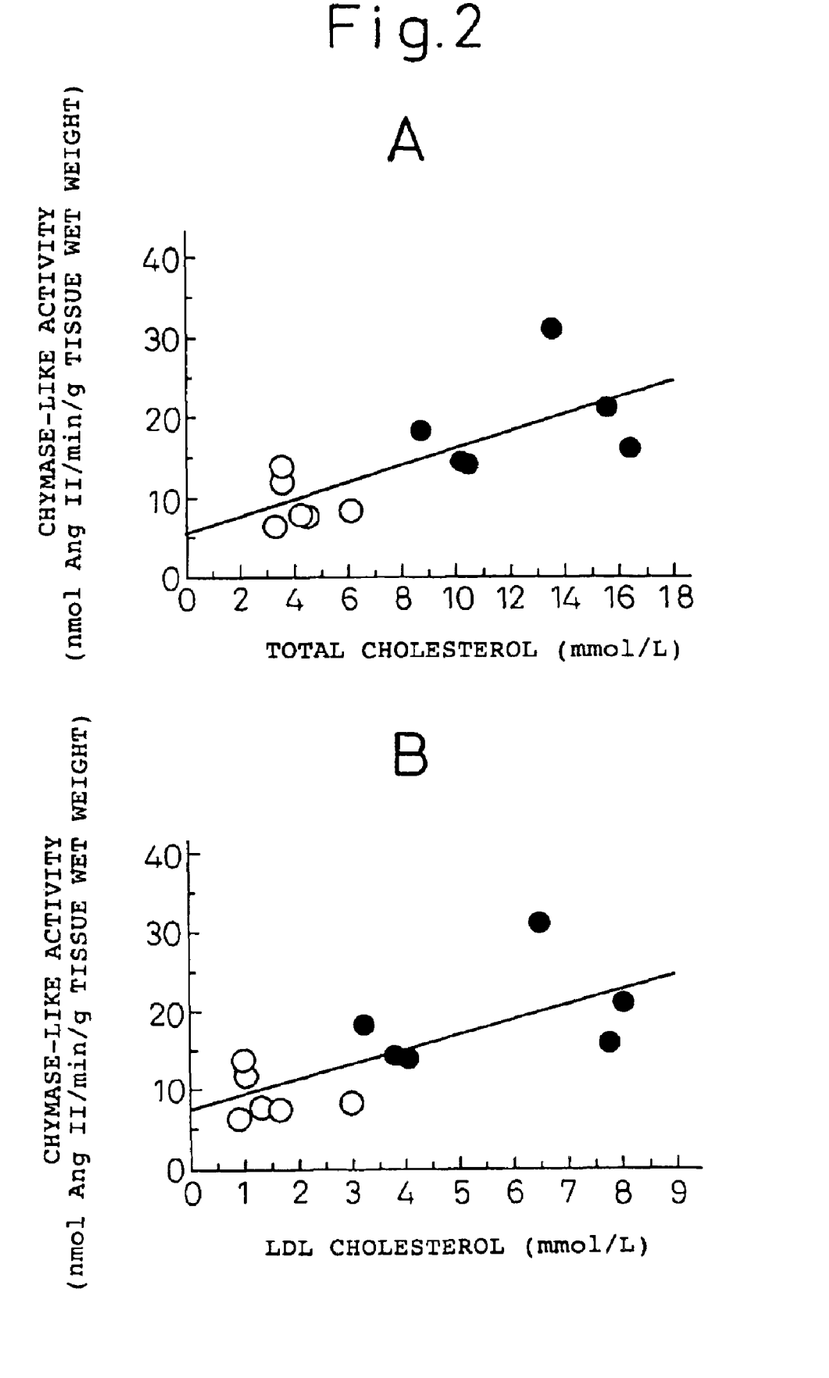
FIG. 2 is a graph showing the correlation between the plasma levels of total cholesterol (A) or LDL-cholesterol (B) and the level of chymase-like activity in a high-cholesterol diet model.

A positive correlation was observed between the chymase-like activity and total cholesterol or LDL cholesterol levels (FIG. 2).

Taken together, these results demonstrate that chymase is involved in lipid deposition induced by a high cholesterol exposure.

Example 4

Construction of Transgenic Mice that Express Human Chymase at a High Level

Transgenic (Tg) mice that express human chymase at a high level were constructed according to the method as described (Zokuseikagakujikkenkoza (Sequel to Biochemistry Experimental Series) 1, Idenshikenkyuhou (Gene Study Method) III, edited by the Japanese Biochemical Society). Briefly, a transgene was generated in which cDNA (J. Biol. Chem. 266: 17173, 1991) encoding human chymase was placed under the control of chicken β actin promoter and the cytomegalovirus immediate early gene promoter. On the next day of mating, fertilized eggs were collected from the oviduct of female mice, and then the above transgene solution was injected into the male pronucleus of the fertilized egg using a thin glass pipet. Fifteen to thirty of these fertilized eggs were transplanted into the oviduct of pseudopregnant female mice, and about 20 days later, the eggs were allowed to undergo the natural or cesarean birth. The newborn mice were bred, and at about 4-week old, DNA was extracted from part of the tail portion, and the presence of the DNA of the introduced gene was searched using Southern blot method (Current Protocols in Molecular Biology, Wiley). The expression of human chymase in each tissue of Tg mice was investigated by Northern blot and Western blot anaylses.

Result:

Tg mice obtained were subjected to spontaneous mating to obtain the offspring (F1) mice, in which the homozygous Tg mice that express human chymase were lethal. On the other hand, naturally born heterozygous Tg mice were found to express human chymase by Northern blot and Western blot in the heart, the blood vessel, the skin, the liver, the lung, and the brain (n=3). The body weight of these Tg mice were slightly smaller than the control mice (wild type littermates) (87% for males and 80% for females, each n=6), and they had hypotrichosis and Leukocytosis (Tg mice had 13300±3600 μl [n=14] relative 7700±2200 μl for the control mice [n=15], p<0.001, t-test). On the other hand, blood pressure of 12-week old Tg mice was about the same level as the control mice (116±15 mmHg [n=10] and 108±9 mmHg [n=10] in Tg mice and the control mice, respectively).

Example 5

Effect of the High-Cholesterol Diet on Human Chymase Tg Mice

Effect of the high-cholesterol diet on the human chymase Tg mice (8-week old each) described in Example 4 was investigated. Preparation of the high-cholesterol diet, the evaluation of lipid deposition in the aorta, and the determination of chymase activity in the aorta were performed in the methods described in Example 6 below.

Figure 3:
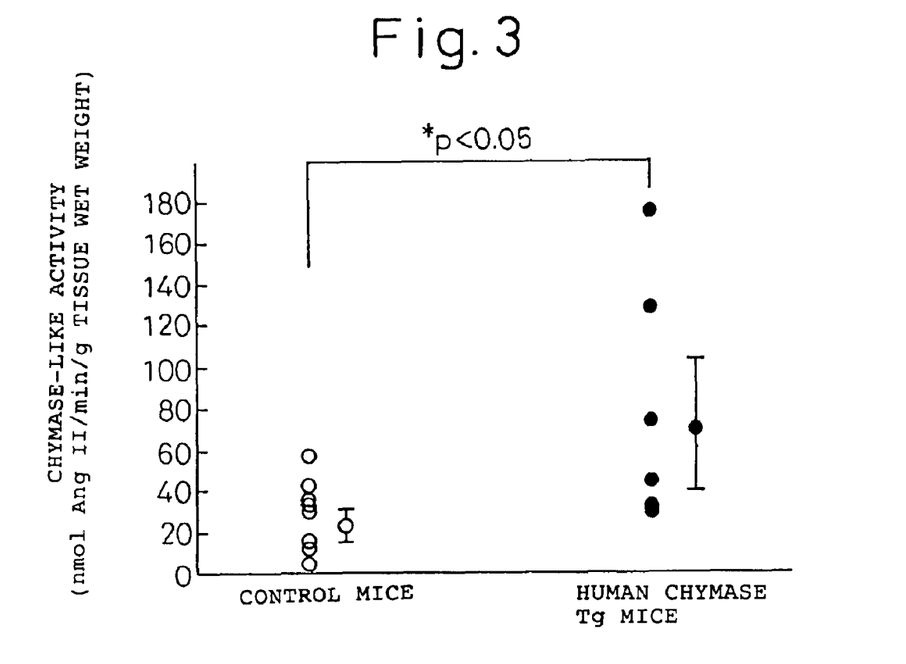
FIG. 3 is a graph showing chymase activity in transgenic (Tg) mice in which human chymase was excessively expressed.
Figure 4:
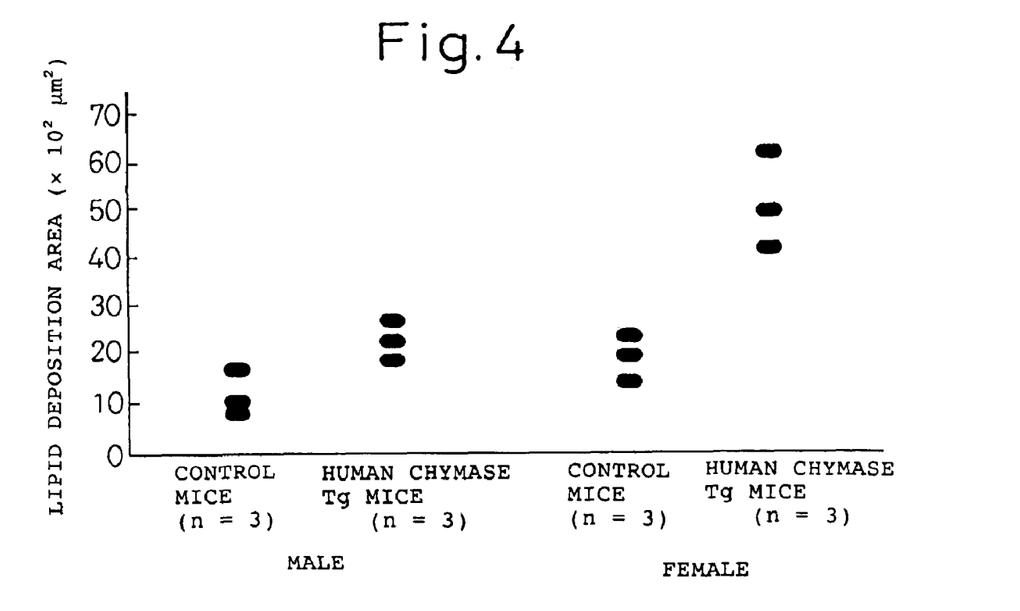
FIG. 4 is a graph showing that arterial lipid deposition in the human chymase Tg mice was significantly higher than that of the control mice when a high cholesterol diet was given.

Result:

Chymase activity in the aorta of the human chymase Tg mice was significantly higher than that of the control mice. (FIG. 3, n=6, p<0.05, t-test). Also, when a high-cholesterol diet is given, a significant increase in the lipid deposition area was observed in the human chymase Tg mice regardless of the sex (FIG. 4, n=3).

The fact that high-cholesterol diet induced lipid deposition in the blood vessel in human chymase Tg mice but not in the control mice indicates the possibility that chymase inhibitor would be effective against lipid deposition on the blood vessel.

Example 6

Effect of Chymase Inhibitor in the Aortic Lipid Deposition Model in Hamster An aortic lipid deposition model was generated as described in Example 3 and used as the high-cholesterol diet group (n=6). A group that received the standard rodent diet for 12 weeks was used as the control group (n=6). The compound obtained in Preparation Example 18 (compound 18) was administered orally to a group that received high-cholesterol diet at a dose of 100 mg/kg/day every day for the same 12 weeks (n=6).

The effect on lipid deposition by the chymase no inhibitor was evaluated by harvesting the aorta on week 12 after the start of the high-cholesterol diet and performing a histopathological analysis. Namely, the ascending aorta from its junction with the heart to the middle part was removed, washed in an ice-cold saline, and then using 3–5 mm segments containing the aortic cusp region were cryopreserved in Tissue-Tek O.C.T. Compound (Miles Inc.). Then, the frozen sections of 6 μm were prepared, fixed in 10% formalin for 10 minutes, washed with distilled water, and then stained with the Oil red O welding (Muto Pure Chemicals) at 60° C. for 5 minutes.

Then, the sections were washed with 60% isopropanol and distilled water, and counterstained with hematoxylin for 2 minutes. After washing with 1/4 saturated LiCO3, lipid deposition was evaluated by microscopic observation. Also, the area of the lipid deposition region (the region stained to an orange color with Oil red O) was quantitated on the histological pictures by NIH Image software ver. 1.61.

Result:

In the microscopic examination of the aortic cusp 12 weeks after the start of the high-cholesterol diet, a conspicuous lipid deposition was observed in the intimal region of the aorta of the hamsters that received the high-cholesterol diet, but lipid deposition had completely disappeared in the aorta of the group that received compound 18. Furthermore, the result in which the area of the lipid deposition region was determined is shown in FIG. 1. The hamsters that received the high-cholesterol diet showed a marked increase in the lipid deposition area in the aortic cusp region as compared to the control group, and the oral administration of compound 18 significantly suppressed the increase in the lipid deposition area.

The finding that compound 18 improves lipid deposition in the high cholesterol-diet model indicates that chymase inhibitor ameliorates the abnormal vascular function to normal, and that chymase inhibitor is useful for the treatment of new diseases accompanied by abnormal vascular function in which lipid deposition in the blood vessel is involved.

Formulation Example 1

Preparation of Tablets

One hundred grams of compound 1 was mixed with 22.5 g of microcrystalline cellulose and 2.5 g of magnesium stearate, which was pressed into tablets by a single punch press to formulate tablets of 9 mm in diameter and 250 mg in weight that contained 200 mg per tablet of compound 1.

Formulation Example 2

Preparation of Granules

Thirty grams of compound 1 was mixed well with 265 g of lactose and 5 g of magnesium stearate, which was compression molded, communicated, sized, and filtered to prepare satisfactory 10% granules of 20–50 mesh.

Formulation Example 3

Preparation of Rectal Suppositories

Witepsol H-15 (manufactured by Dynamit Nobel) was heat-melted, to which compound 1 was added to a concentration of 12.5, mg/ml, mixed into homogeneity. Then this was injected into the die for rectal suppositories in 2 ml portions, and cooled to obtain rectal suppositories containing 25 mg/tablet of compound 1.

INDUSTRIAL APPLICABILITY

According to the present invention, the effect of a chymase inhibitor of suppressing lipid deposition in the blood vessel can effectively prevent or treat diseases accompanied by abnormal vascular function.

What is claimed is:

1. A method for preventing or treating a disease accompanied by abnormal vascular function in which lipid deposition in the blood vessel is involved comprising administering to a patient in need of such prevention or treatment a quinazoline derivative represented by the formula (1):

wherein, the ring A represents an aryl ring, $R^1$ represents a hydroxy group, an amino group, or a lower alkylamino group having 1 to 4 carbons that may be substituted with a carboxylic group, a lower aralkylamino group having 7 to 10 carbons that may be substituted with a carboxylic group, an amino group acylated with a lower fatty acid having 1 to 4 carbons that may be substituted with a carboxylic group, an amino group acylated with an aromatic carboxylic acid that may be substituted with a carboxylic group, an amino group acylated with a heteroaromatic carboxylic acid that may be substituted with a carboxylic group, an amino group sulfonylated with a lower alkanesulfonic acid having 1 to 4 carbons that may be substituted with a carboxylic group, an amino group sulfonylated with an aromatic sulfonic acid that may be substituted with a carboxylic group, an amino group sulfonylated with a heteroaromatic sulfonic acid that may be substituted with a carboxylic group, a lower alkyl group having 1 to 4 carbons substituted with a carboxylic group, or a lower alkylene group having 2 to 4 carbons substituted with a carboxylic group;

$R^2$ and $R^3$, which may be the same or different, represent a hydrogen, a lower alkyl group having 1 to 4 carbons that may be substituted, a halogen atom, a hydroxy group, a lower alkoxy group having 1 to 4 carbons, an amino group, a lower alkylamino group having 1 to 4 carbons that may be substituted, a lower aralkylamino group having 7 to 10 carbons that may be substituted, an amino group acylated with a lower fatty acid having 1 to 4 carbons that may be substituted with a carboxylic group, an amino group acylated with an aromatic carboxylic acid that may be substituted with a carboxylic group, an amino group acylated with a heteroaromatic carboxylic acid that may be substituted with a carboxylic group, an amino group sulfonylated with a lower alkanesulfonic acid having 1 to 4 carbons that may be substituted with a carboxylic group, an amino group sulfonylated with an aromatic sulfonic acid that may be substituted with a carboxylic group, an amino group sulfonylated with a heteroaromatic sulfonic acid that may be substituted with a carboxylic group, or a carboxylic group; or when the ring A is a benzene ring, $R^1$ and $R^2$, together with the benzene ring to be substituted, may form a fused heterocyclic ring that may be substituted with a carboxylic acid, and a carbon atom in said fused heterocyclic ring may form a carbonyl group wherein $R^3$ is as defined above; and X represents a hydrogen atom, a lower alkyl group having 1–4 carbons, a lower alkoxy group having 1 to 4 carbons, a halogen atom, a hydroxy group, an amino group, or a nitro group;

or a pharmaceutically acceptable salt thereof.

2. A method for preventing or treating a disease accompanied by abnormal vascular function in which lipid deposition in the blood vessel is involved, wherein said disease is selected from the group consisting of arteriosclerosis, cardiac acute coronary syndrome, restenosis after percutaneous transluminal coronary angioplasty, obstructive arteriosclerosis, obstructive thrombotic vasculitis, athersclerosis, cerebral infarction, intermittent claudication, lower limb gangrene, renal vascular hypertension, renal arterial aneurysm and renal infarction, comprising administering to a patient in need of such treatment a quinazoline derivative represented by the formula (1):

wherein, the ring represents an aryl ring, $R^1$ represents a hydroxy group, an amino group, or a lower alkylamino group having 1 to 4 carbons that may be substituted with a carboxylic group, a lower aralkylamino group having 7 to 10 carbons that may be substituted with a carboxylic group, an amino group acylated with a lower fatty acid having 1 to 4 carbons that may be substituted with a carboxylic group, an amino group acylated with an aromatic carboxylic acid that may be substituted with a carboxylic group, an amino group acylated with a heteroaromatic carboxylic acid that may be substituted with a carboxylic group, an amino group sulfonylated with a lower alkanesulfonic acid having 1 to 4 carbons that may be substituted with a carboxylic group, an amino group sulfonylated with an aromatic sulfonic acid that may be substituted with a carboxylic group, an amino group sulfonylated with a heteroaromatic sulfonic acid, that may be substituted with a carboxylic group, a lower alkyl group having 1 to 4 carbons substituted with a carboxylic group, or a lower alkylene group having 2 to 4 carbons substituted with a carboxylic group;

$R^2$ and $R^3$, which may be the same or different, represent a hydrogen, a lower alkyl group having 1 to 4 carbons that may be substituted, a halogen atom, a hydroxy group, a lower alkoxy group having 1 to 4 carbons, an amino group, a lower alkylamino group having 1 to 4 carbons that may be substituted, a lower aralkylamino group having 7 to 10 carbons that may be substituted, an amino group acylated with a lower fatty acid having 1 to 4 carbons that may be substituted with a carboxylic group, an amino group acylated with an aromatic carboxylic acid that may be substituted with a carboxylic group, an amino group acylated with a heteroaromatic carboxylic acid that may be substituted with a carboxylic group, an amino group sulfonylated with a lower alkanesulfonic acid having 1 to 4 carbons that may be substituted with a carboxylic group, an amino group sulfonylated with an aromatic sulfonic acid that may be substituted with a carboxylic group, an amino group sulfonylated with a heteroaromatic sulfonic acid that may be substituted with a carboxylic group, or a carboxylic group; or when the ring A is a benzene ring, $R^1$ and $R^2$, together with the benzene ring to be substituted, may form a fused heterocyclic ring that may be substituted with a carboxylic acid, and a carbon atom in said fused heterocyclic ring may form a carbonyl group wherein $R^3$ is as defined above; and X represents a hydrogen atom, a lower alkyl group having 1–4 carbons, a lower alkoxy group having 1 to 4 carbons, a halogen atom, a hydroxy group, an amino group, or a nitro group;

or a pharmaceutically acceptable salt thereof, in an amount effective for treating said diseases accompanied by abnormal vascular function.

3. A method for suppressing lipid deposition in a blood vessel comprising administering to a patient in need of such treatment a quinazoline derivative represented by the formula (1):

(1)

wherein, the ring A represents an aryl ring, $R^1$ represents a hydroxy group, an amino group, or a lower alkylamino group having 1 to 4 carbons that may be substituted with a carboxylic group, a lower aralkylamino group having 7 to 10 carbons that may be substituted with a carboxylic group, an amino group acylated with a lower fatty acid having 1 to 4 carbons that may be substituted with a carboxylic group, an amino group acylated with an aromatic carboxylic acid that may be substituted with a carboxylic group, an amino group acylated with a heteroaromatic carboxylic acid that may be substituted with a carboxylic group, an amino group sulfonylated with a lower alkanesulfonic acid having 1 to 4 carbons that may be substituted with a carboxylic group, an amino group sulfonylated with an aromatic sulfonic acid that may be substituted with a carboxylic group, an amino group sulfonylated with a heteroaromatic sulfonic acid that may be substituted with a carboxylic group, a lower alkyl group having 1 to 4 carbons substituted with a carboxylic group, or a lower alkylene group having 2 to 4 carbons substituted with a carboxylic group;

$R^2$ and $R^3$, which may be the same or different, represent a hydrogen, a lower alkyl group having 1 to 4 carbons that may be substituted, a halogen atom, a hydroxy group, a lower alkoxy group having 1 to 4 carbons, an amino group, a lower alkylamino group having 1 to 4 carbons that may be substituted, a lower aralkylamino group having 7 to 10 carbons that may be substituted, an amino group acylated with a lower fatty acid having 1 to 4 carbons that may be substituted with a carboxylic group, an amino group acylated with an aromatic carboxylic acid that may be substituted with a carboxylic group, an amino group acylated with a heteroaromatic carboxylic acid that may be substituted with a carboxylic group, an amino group sulfonylated with a lower alkanesulfonic acid having 1 to 4 carbons that may be substituted with a carboxylic group, an amino group sulfonylated with an aromatic sulfonic acid that may be substituted with a carboxylic group, an amino group sulfonylated with a heteroaromatic sulfonic acid that may be substituted with a carboxylic group, or a carboxylic group; or when the ring A is a benzene ring, $R^1$ and $R^2$, together with the benzene ring to be substituted, may form a fused heterocyclic ring that may be substituted with a carboxylic acid, and a carbon atom in said fused heterocyclic ring may form a carbonyl group wherein $R^3$ is as defined above; and X represents a hydrogen atom, a lower alkyl group having 1–4 carbons, a lower alkoxy group having 1 to 4 carbons, a halogen atom, a hydroxy group, an amino group, or a nitro group;

or a pharmaceutically acceptable salt thereof, in an amount effective for suppressing lipid deposition in the blood vessel.

\* \* \* \* \*